United States Patent

Eberle et al.

[11] Patent Number: 5,453,427
[45] Date of Patent: Sep. 26, 1995

[54] PYRIMIDINYL ACRYLIC ACID DERIVATIVES

[75] Inventors: Martin Eberle, Bottmingen; Fritz Schaub, Aesch; Gerald W. Craig, Basle, all of Switzerland

[73] Assignee: Sandoz Ltd., Basle, Switzerland

[21] Appl. No.: 273,033

[22] Filed: Jul. 8, 1994

[30] Foreign Application Priority Data

Jul. 12, 1993 [GB] United Kingdom ............. 9314355

[51] Int. Cl.$^6$ ............. C07D 239/34; C07D 239/42; C07D 239/52; A01N 43/54
[52] U.S. Cl. ............. 514/269; 514/252; 514/259; 514/272; 514/274; 544/284; 544/295; 544/296; 544/238; 544/310; 544/319; 544/320; 544/321
[58] Field of Search ............. 514/269, 272, 514/274, 252, 259, 269; 544/315, 316, 318, 319, 320, 321, 284, 295, 296, 238, 310

[56] References Cited

FOREIGN PATENT DOCUMENTS

| 243012 | 4/1986 | European Pat. Off. |
| 312243 | 10/1987 | European Pat. Off. |
| 383117 | 2/1989 | European Pat. Off. |
| 471261 | 8/1990 | European Pat. Off. |
| 471262 | 8/1990 | European Pat. Off. |

Primary Examiner—John M. Ford
Attorney, Agent, or Firm—Lynn Marcus-Wyner; Allen E. Norris

[57] ABSTRACT

The invention discloses compounds of formula I It has now been found that compounds of formula I

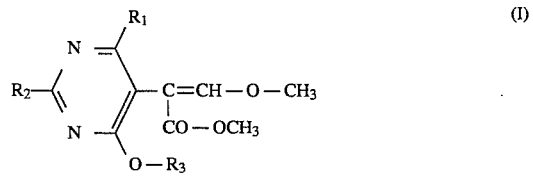

wherein
$R_1$ is hydrogen, methyl, ethyl or trifluoromethyl, and
$R_2$ is hydrogen, methyl, ethyl, $C_{1-4}$alkylthio, $C_{1-4}$alkoxy, or di-$C_{1-4}$alkylamino, and
$R_3$ is $C_{1-10}$alkyl, $C_{1-10}$haloalkyl, aryl, heteroaryl, aryl-$C_{1-4}$alkyl, heteroaryl-$C_{1-4}$alkyl, aryloxy-$C_{1-4}$alkyl, aryloxyaryl, arylaryl, heteroaryl, aryl-$C_{1-4}$alkoxyaryl, aryl-$C_{1-4}$alkoxy-$C_{1-4}$alkyl, heteroaryloxyaryl, aryloxy-$C_{1-4}$alkylaryl or aryl substituted by a group selected from —C(CH$_3$)=N—O—CH$_2$—aryl, —C(CH$_3$)=N—O—CH(CH$_3$)—aryl, —C(CH$_3$)=N—C$_{1-4}$ alkoxy, —C(CH$_3$)=N—C$_{3-4}$alkenyloxy,—C(CH$_3$)=N—C$_{3-4}$alkynyloxy, or —CH$_2$—O—N=C(CH$_3$)—aryl, wherein each of the aromatic rings may be optionally substituted; the use of such compounds for the control of phytopathogens, compositions for facilitating such use, and the preparation of the compounds of fomula I.

19 Claims, No Drawings

PYRIMIDINYL ACRYLIC ACID DERIVATIVES

This invention relates to novel α-pyrimidinyl acrylic acid derivatives, the synthesis thereof and the use of said compounds for the control of phytopathogens.

α-(Pyrid-3-yl)-β-methoxy acrylates are known from EP-A-0243012. Said compounds have been proposed as agricultural/horticultural fungicides. These compounds do however not provide satisfactory control of phytopathogenic fungi under all aspects.

It has now been found that compounds of formula I

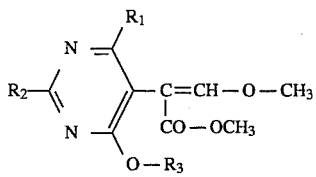

wherein $R_1$ is hydrogen, methyl, ethyl or trifluoromethyl, and
$R_2$ is hydrogen, methyl, ethyl, $C_{1-4}$alkylthio, $C_{1-4}$alkoxy, or di-$C_{1-4}$alkylamino, and
$R_3$ is $C_{1-10}$alkyl, $C_{1-10}$haloalkyl, aryl, heteroaryl, aryl-$C_{1-4}$alkyl, heteroaryl-$C_{1-4}$alkyl, aryloxy-$C_{1-4}$alkyl, aryloxyaryl, arylaryl, heteroarylaryl, aryl-$C_{1-4}$alkoxyaryl, aryl-$C_{1-4}$alkoxy-$C_{1-4}$alkyl, heteroaryloxyaryl, aryloxy-$C_{1-4}$alkylaryl or aryl substituted by a group selected from —C(CH$_3$)=N—O—CH$_2$aryl, —C(CH$_3$)=N—O—CH(CH$_3$)—aryl, —C(CH$_3$)=N—C$_{1-4}$alkoxy, —C(CH$_3$)=N—C$_{3-4}$alkenyloxy, —C(CH$_3$)=N—C$_{3-4}$alkynyloxy, or —CH$_2$—O—N=C(CH$_3$)—aryl, wherein each of the aromatic rings may be optionally substituted, are surprisingly effective against phytopathogens.

In the definitions of the radicals $R_2$ and $R_3$ of formula I alkyl is understood to encompass straight-chain and branched alkyl groups, with straight-chain and lower alkyl being preferred. For example alkyl is methyl, ethyl, n-propyl, isopropyl, n-butyl, isobutyl, tertiary butyl or secondary butyl, and the various isomers of pentyl, hexyl, heptyl, octyl, nonyl and decyl.

The alkyl portion of alkylthio, alkoxy, haloalkyl, alkylamino, or radicals under the definition of $R_3$ which comprise alkyl as part of the radical, in this document shall have the same given meanings.

Alkenyl designates allyl, methallyl, 3-butenyl, 2-butenyl, with allyl being preferred. Alkynyl designates propergyl, 2-butynyl, 3-butynyl, with propergyl being preferred.

Haloalkyl designates straight chain or branched alkyl groups which are mono- to perhalogenated with straight-chain lower alkyl being the preferred alkyl and with fluorine and chlorine being preferred halogens. Examples are trifluoromethyl, difluoromethyl, 2,2,2-trifluoroethyl or 2,2,3,3,3-pentafluoropropyl.

Aryl stands for aromatic hydrocarbon radicals, for example phenyl or naphthyl, with phenyl being preferred.

Heteroaryl stands for aromatic 5- or 6-membered cyclic radicals comprising one, two or three ring atoms selected from nitrogen, oxygen and sulfur, which may also be in condensed form with another heteroaryl radical or aryl radical. Examples are pyridyl, pyrimidinyl, pyridazinyl, quinolinyl, quinazolinyl, thienyl, or furyl. The heteroaryl radicals are linked to the basic structure of formula I through a carbon ring atom.

In radicals being combined from various other definitions, each of the definitions has the meanings given for the partial definition separately.

Arylalkyl and heteroarylalkyl designate an aryl or heteroaryl radical being linked to an alkylene chain through a carbon atom. Typical examples are benzyl, phenylethyl, 3-phenylpropyl, furfuryl, or 3-pyridylmethyl.

Aryloxyalkyl and heteroaryloxyalkyl designate an aryloxy or heteroaryloxy radical being linked to an alkylene chain through an oxygen atom. Typical examples are phenoxyethyl, 2-phenoxypropyl, 2- or 3-pyridyloxymethyl, 2- or 3- pyridyloxyethyl or phenoxymethyl.

Aryloxyaryl or heteroaryloxyaryl designate and aryloxy or heteroaryloxy radical being linked through the oxygen atom to an aryl radical. Examples are phenoxyphenyl, pyridyloxyphenyl, quinolinoxyphenyl, pyrimidinyloxyphenyl or pyridazinyloxyphenyl.

Heteroarylaryl designates a heteroaryl radical being linked to an aryl through a carboncarbon bond. Examples are pyridylphenyl, thienylphenyl or furylphenyl.

Arylaryl designates an aryl radical being linked to another aryl radical through a carboncarbon bond. Examples are biphenyl or naphthylphenyl.

Arylalkoxyalkyl stands for an arylalkoxy radical being linked to an alkylene chain through the oxygen atom. Examples are benzyloxyethyl, benzyloxypropyl, benzyloxybutyl, phenylethyloxyethyl or phenylethyloxypropyl.

Arylalkoxyaryl designates an arylalkoxy radical being linked to another aryl ring through the oxygen atom. Examples are benzyloxyphenyl, 2-phenylethoxyphenyl, 1-phenylethoxyphenyl or phenylpropoxyphenyl.

Aryloxyalkylaryl stand for an aryloxy radical being linked to another aryl radical through an alkylene chain. Examples are phenoxymethylphenyl, phenoxyethylphenyl or phenoxypropylphenyl.

The above radicals may be further substituted in the aliphatic or aromatic portion of the complete group, with the substitution in the aromatic portion being preferred.

Where $R_3$ is an optionally substituted radical it is preferably substituted by one to five radicals independently selected from the group comprising halogen, $C_{1-4}$alkyl, $C_{1-4}$alkoxy, $C_{3-7}$cycloalkyl, $C_{1-4}$haloalkyl, $C_{1-4}$haloalkoxy, cyano, nitro, aryl, aryloxy or aryl-$C_{1-4}$alkoxy. More preferred is substitution by one or two independently selected radicals.

Halogen is fluorine, chlorine, bromine or iodine, with fluorine and chlorine being preferred.

The alkyl portions of alkoxy, alkylthio, haloalkyl, haloalkoxy, and arylalkoxy are as defined for alkyl, while the aryl portions of aryloxy and arylalkoxy are as defined for aryl. Typical examples for alkoxy are methoxy, ethoxy, n-propoxy, isopropoxy or the isomers of butoxy. Examples for haloalkyl are trifluoromethyl, fluoromethyl, chloromethyl, difluoromethyl, 2-chloroethyl, 2-fluoromethyl, 2,2,2-trifluoroethyl or 1,2,2,2-tetrafluoroethyl. Examples for haloalkoxy are trifluoromethoxy, difluoromethoxy, 1,1,2,2-tetrafluoroethoxy, 2,2,2-trifluoroethoxy or 2-chloroethoxy. Examples for aryloxy are phenoxy or naphthyloxy. Examples for arylalkoxy are benzyloxy or phenylethoxy. Examples for alkylthio are methylthio, ethylthio, propylthio, isopropylthio or butylthio.

Cycloalkyl stands for cyclopropyl, cyclobutyl, cyclopentyl, cyclohexyl or cycloheptyl, with cyclohexyl and cyclopentyl being preferred.

A preferred subgroup of compounds of formula I is characterized wherein $R_3$ is $C_{1-10}$alkyl, phenyl, naphthyl, pyridyl, pyrimidinyl, thienyl, furyl, benzyl, phenethyl, phenoxy-$C_{1-4}$alkyl, or benzyloxy-$C_{1-4}$alkyl wherein each of the aromatic cyclic moiety is optionally substituted by one or two substituents selected from the group consisting of halogen, $C_{1-4}$alkyl, $C_{1-4}$alkoxy, $C_{1-4}$haloalkyl, $C_{1-4}$haloalkoxy, cyano, nitro, aryloxy, aryl-$C_{1-4}$alkoxy, and aryl. In the case of substitution with halogen atoms, also more than two substituents may be present, e.g. in pentaflorophenyl, trichlorophenyl, tetrachlorophenyl, pentachlorophenyl, tetrafluorophenyl or trifluorophenyl. Among this group especially those compounds are preferred wherein $R_3$ is $C_{1-4}$alkyl, phenyl, benzyl, phenoxyethoxy, benzyloxyethoxy, biphenyl, $C_{1-4}$alkylphenyl, $C_{1-4}$haloalkylphenyl, or halophenyl.

Further preferred subgroups comprise compounds of formula I, wherein $R_2$ is hydrogen, or wherein $R_1$ is methyl.

A specially preferred group of compounds of formula I is characterized wherein $R_1$ is methyl, $R_2$ is hydrogen and $R_3$ is $C_{1-4}$alkyl, phenyl, benzyl, phenoxyethoxy, benzyloxyethoxy, biphenyl, $C_{1-4}$alkylphenyl, $C_{1-4}$haloalkylphenyl, or halophenyl.

Another preferred subgroup of compounds of corresponds to the subformula Ia

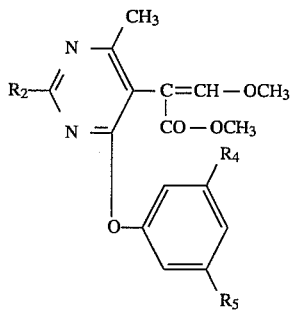

(Ia)

wherein
$R_2$ is hydrogen, methyl or methylthio,
$R_4$ is hydrogen or methyl, and
$R_5$ is hydrogen, aryl, heteroaryl, $C_{1-4}$alkyl, —$CH_2$—O—$C_{1-4}$alkyl, —$CH_2$—O—$C_{3-7}$cycloalkyl, —$CH_2$—O—aryl, —$CH_2$—O—$CH_2$—aryl, —$C(CH_3)$=N— $C_{1-4}$alkoxy, —$C(CH_3)$=N—$C_{3-4}$alkenyloxy, —$C(CH_3)$=N—$OCH_2$—aryl, wherein aryl may be optionally substituted by one or two radicals independently selected from halogen, $C_{1-4}$alkyl, $C_{1-4}$alkoxy or cyano, or is 2-pyridyloxy optionally substituted by one or two radicals independently selected from $C_{1-4}$alkyl, halogen or nitro; or is phenoxy optionally substituted by one to three radicals selected from $C_{1-4}$alkyl, cyano, nitro, halogen, $C_{1-4}$haloalkyl, $C_{1-4}$alkoxy, or $C_{1-4}$haloalkoxy; or is benzyloxy optionally substituted by one to five radicals independently selected from halogen or $C_{1-4}$alkyl, or one to three radicals independently selected from halogen, $C_{1-4}$alkyl, nitro, $C_{1-4}$haloalkoxy or cyano.

Among the compounds of formula Ia those are preferred wherein $R_5$ is hydrogen, phenyl, thienyl, $C_{1-4}$alkyl, phenoxymethyl, —$C(CH_3)$=N—$OCH_3$, phenoxy, benzyloxy, —$C(CH_3)$=N-allyloxy, —$C(CH_3)$=N-benzyloxy, wherein the phenyl groups are optionally substituted by one or two substituents independently selected from cyano, methyl, trifluoromethyl, methoxy, nitro or halogen, especially chlorine.

Preferred individual compounds of formula I are:
methyl α-[6-methyl-4-(3-trifluoromethylphenoxy)-5-pyrimidinyl]-β-methoxyacrylate;
methyl α-[6-methyl-4-(3-(2-cyanophenoxy)-phenoxy)-5-pyrimidinyl]-β-methoxyacrylate;
methyl α-[6-methyl-4-(3-(1-methoximinoethyl)-phenoxy)-5-pyrimidinyl]-β-methoxyacrylate;
methyl α-[6-methyl-4-(3-isopropylphenoxy)-5-pyrimidinyl]-β-methoxyacrylate;

methyl α-[6-methyl-4-(3-phenylphenoxy)-5-pyrimidinyl]-β-methoxyacrylate;
methyl α-[2-methyl-4-(3-trifluoromethylphenoxy)-5-pyrimidinyl]-β-methoxyacrylate;
methyl α-[2-methylthio-6-methyl-4-(3-trifluoromethylphenoxy)-5-pyrimidinyl]-β-methoxyacrylate;
methyl α-[2,6-dimethyl-4-(3-phenylphenoxy)-5-pyrimidinyl]-β-methoxyacrylate;
methyl α-[2,6-dimethyl-4-(3-methyl-5-isopropylphenoxy)-5-pyrimidinyl]-β-methoxyacrylate; and
methyl α-[6-methyl-4-(3-(2-methylbenzyloxy)-phenoxy)-5-pyrimidinyl]-β-methoxyacrylate.

The double bond of the acrylic acid structure in the compounds of formula I may be in E- or Z-form. In .this document the E- and Z-forms are identified where meant specifically. In all other cases mixtures of the two isomers are intended. Where E- and Z-isomers are obtained during synthesis they may be separated by known techniques, such as crystallisation, chromatography or destillation. In the described methods of preparation preferably the E-forms are obtained.

Compounds of formula I may be obtained by O-methylation of a compound of formula II

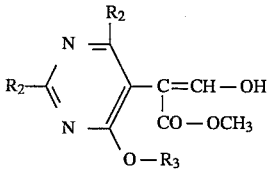

(II)

wherein $R_1$, $R_2$ and $R_3$ are as defined above.

The O-methylation can be carried out in a manner known per se for the preparation of 3-methoxyacrylates employing conventional methylation agents. Examples of suitable methylation agents include methyl iodide and dimethyl sulphate. The O-methylation is conveniently carried out in the presence of a base. The reaction temperature will conveniently lie in the range of from 0° C. to the boiling point of the reaction mixture, e.g. at about ambient temperature. Inert solvents may be used where desired. Examples of suitable bases include alkaline metal hydroxides such as sodium hydroxide, alkaline metal hydrides such as sodium hydride, alkaline metal alcoholates such as sodium methylate, alkaline metal carbonates or alkaline metal hydrogen carbonate such as potassium carbonate or sodium hydrogen carbonate. Examples of suitable inert solvents include aromatic hydrocarbons such as benzene and toluene; ethers such as diethyl ether, tetrahydrofuran and 1,2-dimethoxyethane; polar solvents such as dimethylformamide, dimethyl sulfoxide, water, alcohols such as methanol; acetone or a mixture comprising two or more of them. The desired end-product is isolated and purified according to known techniques, for example by evaporation of solvent, chromatography and crystallisation. The compounds of formula I are basic in nature. They may form salts with sufficiently strong acids such as HCl and HBr.

The compounds of formula II may be obtained by reaction of compounds of formula III

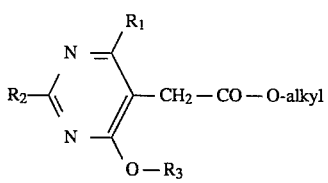

wherein $R_1$, $R_2$ and $R_3$ are as defined above and alkyl is $C_{1-10}$alkyl, with methyl formate in the presence of a base.

This reaction is essentially a Claisen reaction and may be carried out under the conditions known for such reaction. The reaction (III→II) may be carried out in an inert solvent. Examples of suitable solvents are as described for the O-methylation of the compounds of formula (II). Examples of suitable bases are such typically used for a Claisen reaction such as alkaline metal alcoholates, e.g. sodium methylate; alkaline metal hydrides, e.g. sodium hydride; and alkaline metal carbonates, e.g. sodium carbonate or potassium carbonate. The reaction temperature may vary within wide ranges, e.g. from 0° C. to the boiling point of the reaction mixture and is preferably at or near ambient temperature.

The acetic acid esters of formula 121I may be obtained from compounds of formula IV

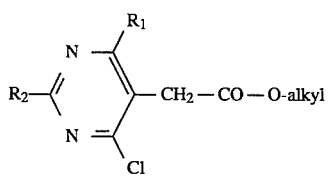

wherein $R_1$ and $R_2$ are as defined above, by reacting it with an alcohol of formula V

wherein $R_3$ is as defined above in the presence of a base and an inert solvent. Suitable bases and solvents are as for (II→I).

Compounds of formula III wherein $R_2$ is H may alternatively be obtained by reacting a compound of fomula VI

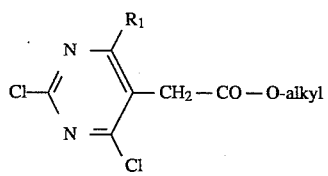

wherein $R_1$ is as defined above, with an alcohol of formula V in the presence of a base and an inert solvent, and hydrogenating the obtained intermediate of formula VII

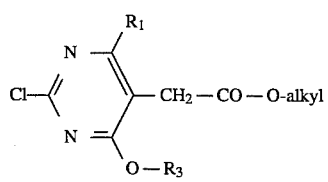

wherein $R_1$ and $R_3$ are as defined above. Hydrogenation is carried out in a manner known per se. Typical procedures would be hydrogenation in the presence of a suitable noble metal catalyst, e.g. palladium/charcoal, or treatment with hydroiodic acid, or treatment with sodium borohydride. The reaction conditions for the first step (VI+V → VII) are identical to the conditions of (IV+V→III). The hydrogenation step (VII→III) correspond to typical reaction conditions known in the art for these types of reactions.

Compounds of formula IV wherein $R_2$ is $C_{1-4}$alkylthio may also be obtained by reacting a compound of formula VIII

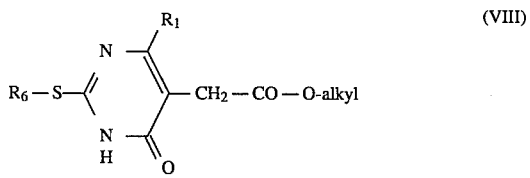

wherein $R_6$ is $C_{1-4}$alkyl and $R_1$ and alkyl are as defined above, with a chlorinating agent, such as $POCl_3$.

The compounds of formula VIII may in turn be obtained from a starting material of formula IX

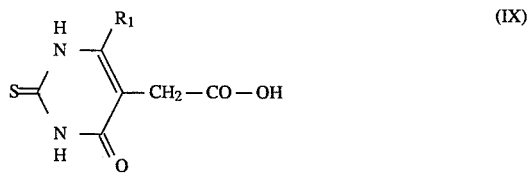

wherein $R_1$ is as defined above, by esterification, i.e. with an alcohol HO-alkyl in the presence of an acid such as $H_2SO_4$ or HCl, and alkylating the obtained intermediate of formula X

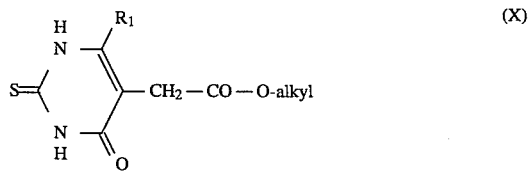

wherein $R_1$ and alkyl are as defined above, in the presence of a base, such as NaOH with an alkylhalogenid of formula XI

wherein Hal is bromine or chlorine and $R_6$ is as defined above.

Compounds of formula III wherein $R_2$ is H may according to another variant be prepared by desulfurating the intermediate of formula X in the presence of desulfurating catalyst such as Raney-Nickel and reacting the obtained intermediate of formula XII

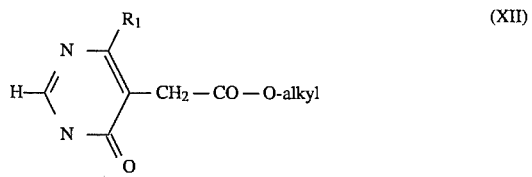

with a chlorinating agent, such as $POCl_3$.

In an alternative process the compounds of formula II may also be obtained by reacting the compounds of formula III with a 1:1-adduct of dimethylformamide and dimethyl-sulfate in the presence of a strong base, such as t-BuOK and hydrolysing the obtained intermediate of formula XIII

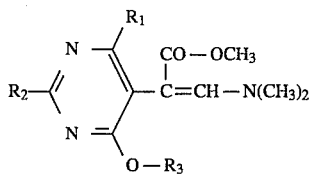

wherein $R_1$, $R_2$ and $R_3$ are as defined above.

The starting materials of formulae IV, V, VI, IX and XI are known or may be prepared in analogy to known processes.

The compounds of formula (I) are effective against phytopathogens.

Their advantageous fungicidal activity is established by in vivo tests with test concentrations from 0.1 to 500 mg a.i./l against Uromyces appendiculatus on pole beans, against *Puccinia triticina* on wheat, against *Sphaerotheca fuliginea* on cucumber, against *Erysiphe graminis* on wheat and barley, against *Podosphaera leucotricha* on apple, against Uncinula necator on grape vine, against *Leptosphaeria nodorum* on wheat, against *Cochliobolus sativus* and *Pyrenophora graminca* on barley, against *Venturia inaequalis* on apple, against Phytophthora infestans on tomato and against *Plasmopara viticola* on grape vine.

Many of the compounds of formula (I) have an excellent plant tolerance and a systemic action. The compounds of the invention are therefore indicated for treatment of plant, seeds and soil to combat phytopathogenic fungi, e.g. Basidiomycetes of the order Uredinales (rusts) such as Puccinia spp, Hemileia spp, Uromyces spp; and Ascomycetes of the order Erysiphales (powdery mildew) such as Erysiphe ssp, Podosphaera spp, Uncinula spp, Sphaerotheca spp; as well as Cochliobolus; Pyrenophora spp; Venturia spp; Mycosphaerella spp; Leptosphaeria; Deuteromycetes such as Pyricularia, Pellicularia (Corticium), Botrytis; and Oomycetes such as Phytophthora spp, Plasmopara spp.

The compounds of formula (I) are particularly effective against powdery mildew and rust, pyrenophora and leptosphaeria fungi, in particular against pathogens of monocotyledoneous plants such as cereals, including wheat and barley.

The amount of compound of the invention to be applied, will depend on various factors such as the compound employed, the subject of the treatment (plant, soil, seed), the type of treatment (e.g. spraying, dusting, seed dressing), the purpose of the treatment (prophylactic or therapeutic), the type of fungi to be treated and the application time.

In general, satisfactory results are obtained, if the compounds of the invention are applied in an amount of from about 0.0005 to 2.0, preferably about 0.01 to 1 kg/ha, in the case of a plant or soil treatment; e.g. 0.04 to 0.500 kg of active ingredient (a.i.) per ha in field crops such as cereals, or concentrations of 4 to 50 g of a.i. per hl in crops such as fruits, vineyards and vegetables (at an application volume of from 300 to 1000 l/ha—depending on the size or leaf volume of the crop—which is equivalent to an application rate of approximately 30–500 g/ha). The treatment can, if desired, be repeated, e.g. at intervals of 8 to 30 days.

Where the compounds of the invention are used for seed treatment, satisfactory results are in general obtained, if the compounds are used in an amount of from about 0.05 to 0.5, preferably about 0.1 to 0.3 g/kg seeds.

The term soil as used herein is intended to embrace any conventional growing medium, whether natural or artificial.

The compounds of the invention may be used in a great number of crops, such as soybean, coffee, ornamentals (i.a. pelargonium, roses), vegetables (e.g. peas, cucumber, celery, tomato and bean plants), sugarbeet, sugarcane, cotton, flax, maize (corn), vineyards, pomes and stone fruits (e.g. apple, pears, prunes) and in cereals (e.g. wheat, oats, barley, rice).

The invention also provides fungicidal compositions, comprising as a fungicide a compound of formula I in association with a agriculturally acceptable diluent (hereinafter diluent). They are obtained in conventional manner, e.g. by mixing a compound of the invention with a diluent and optionally additional ingredients, such as surfactants.

The term diluents as used herein means liquid or solid agriculturally acceptable material, which may be added to the active agent to bring it in an easier or better applicable form, resp. to dilute the active agent to a usable or desirable strength of activity. Examples of such diluents are talc, kaolin, diatomaceous earth, xylene or water.

Especially formulations used in spray form, such as water dispersible concentrates or wettable powders, may contain surfactants such as wetting and dispersing agents, e.g. the condensation product of formaldehyde with naphthalene sulphonate, an alkylarylsulphonate, a lignin sulphonate, a fatty alkyl sulphate, an ethoxylated alkylphenol and an ethoxylated fatty alcohol.

In general, the formulations include from 0.01 to 90% by weight of active agent, from 0 to 20% agriculturally acceptable surfactant and from 10 to 99.99% diluent(s).

Concentrated forms of composition, e.g. emulsion concentrates, contain in general from about 2 to 90%, preferably from between 5 and 70% by weight of active agent. Application forms of formulation contain in general from 0.0005 to 10% by weight of a compound of the invention as active agent typical spray-suspensions may, for example, contain from 0.0005 to 0.05, e.g. 0.0001, 0.002 or 0.005% by weight of active agent.

In addition to the usual diluents and surfactants, the compositions of the invention may comprise further additives with special purposes, e.g. stabilisers, desactivators (for solid formulations or careers with an active surface), agents for improving the adhesion to plants, corrosion inhibitors, anti-foaming agents and colorants. Moreover, further fungicides with similar or complementary fungicidal activity, e.g. sulphur, chlorothalonil, euparen; a guanidine fungicide such as guazatine; dithiocarbamates such as mancozeb, maneb, zineb, propineb; trichloromethane sulphenylphthalimides and analogues such as captan, captafol and folpet; benzimidazoles such as carbendazim, benomyl; azoles such as cyproconazole, flusilazole, flutriafol, hexaconazole, propiconazole, tebuconazole, epoxiconazole, tritiiconazole, prochloraz; morpholines such as fenpropimorph, fenpropidine, or other beneficially-acting materials, such as cymoxanil, oxadixyl, metalaxyl, or insecticides may be present in the formulations.

Examples of plant fungicide formulations are as follows:
a. Wettalkie Powder Formulation 10 Parts of a compound of formula I are mixed and milled with 4 pans of synthetic fine silica, 3 pans of sodium lauryl sulphate, 7 parts of sodium lignin sulphonate and 66 parts of finely divided kaolin and 10 parts of diatomaceous earth until the mean particle size is about 5 micron. The resulting wettable powder is diluted with water before use to a spray liquor which may be applied by foliar spray as well as by root drench application.

b. Granules

Onto 94.5 parts by weight of quartz sand in a tumbler mixer are sprayed 0.5 parts by weight of a binder (non-ionic tenside) and the whole thoroughly mixed. 5 parts by weight of a compound of formula I invention are then added and thorough mixing continued to obtain a granulate formulation with a particle size in the range of from 0.3 to 0.7 mm (where required, the granules may be dried by the addition of 1 to 5 % by weight of talcum). The granules may be applied by incorporation into the soil adjacent to the plants to be treated.

c. Emulsion Concentrate

10 Parts by weight of a compound of formula I are mixed with 10 parts of weight of an emulsifier and 80 parts by weight of xylene. The thus obtained concentrate is diluted with water to form an emulsion of the desired concentration, prior to application.

d. Seed Dressing

45 Parts of a compound of formula I are mixed with 1.5 parts of diamyl phenoldecaglycolether ethylene oxide adduct, 2 parts of spindle oil, 51 parts of fine talcum and 0.5 parts of colorant rhodanin B. The mixture is ground in a contraplex mill at 10,000 rpm until an average particle size of less than 20 microns is obtained. The resulting dry powder has good adherence and may be applied to seeds, e.g. by mixing for 2 to 5 minutes in a slowly turning vessel.

The following examples further illustrate the present invention. All temperatures are in centigrade. Rf values are obtained by thin layer chromatography on silica gel, unless otherwise specified.

EXAMPLE 1

Methyl α-[2-methyl-4-(3-trifluoromethylphenoxy)-5-pyrimidinyl]-β-methoxyacrylate

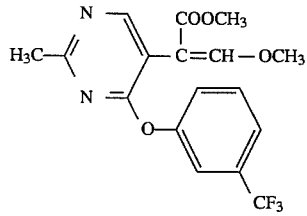

a) Ethyl α[2-methyl-4-(3-trifluoromethylphenoxy)-5-pyrimidinyl]-acetate

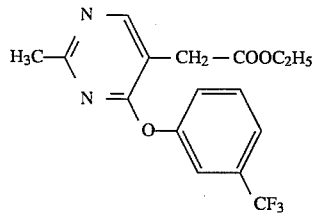

Ethyl α-(2-methyl-4-chloro-5-pyrimidinyl)-acetate (3 g, 14 mmol), 3-trifluoromethyl phenol (3 g, 14 mmol) and potassium carbonate (11 g, 80 mmol) in dimethylformamide (50 ml) are stirred at +80° C. for 3 hours. The mixture is diluted with ether and washed with brine. Drying over MgSO₄ and evaporation of the solvent gives pure ethyl α-[2-methyl-4-(3-trifluoromethylphenoxy)-5-pyrimidinyl] acetate as an oil.

¹H (CDCl₃): 8.36 (s, 1H); 7.50-7.25 (m, 4H); 3.90 (s, 2H); 3.85 (s, 3H); 2.5 (s,3H).

b) Ethyl α-[2-methyl-4-(3-trifluoromethylphenoxy)-5-pyrimidinyl]-acetate (3 g, 8 mmol) are dissolved in methyl formate (10 ml) and added to a suspension of NaH (0.6 g, 80% in oil, 20 mmol) in 1,2-dimethoxyaethane at room temperature. After 16 hours methyl iodide (2.5 ml, 40 mmol) is added with cooling. After further 2 hours the reaction mixture is diluted with ether and washed with brine. Drying and chromatography on silicagel (eluant: hexane/ethyl acetate 1:1) gives the methyl α-[ 2-methyl-4-(3-trifluoromethylphenoxy)-5-pyrimidinyl]-β-methoxyacrylate compound as a crystalline solid, m.p. 100°–102° C.

EXAMPLE 2

Methyl α-[6-methyl-4-(3-phenylphenoxy)-5-pyrimidinyl]-β-methoxyacrylate

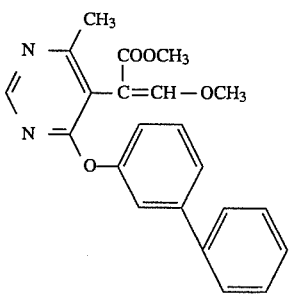

a) Methyl α-[6-methyl-2-chloro-4-(3-phenylphenoxy)-5-pyrimidinyl]-acetate

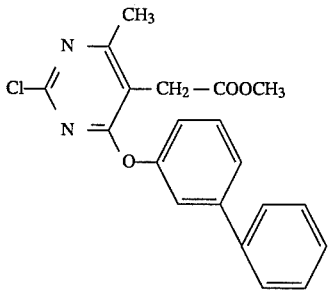

Methyl α-[6-methyl-2,4-dichloro-5-pyrimidinyl]-acetate (4 g, 18 mmol), 3-hydroxybiphenyl (3 g, 18 mmol) and potassium carbonate (11 g, 80 mmol) in dimethylformamide (50 ml) are stiffed at +80° C. for 2 hours. Workup as for example 1a) gives pure methyl α-[6-methyl-2-chloro-4-(3-phenylphenoxy)-5 -pyrimidinyl]-acetate.

¹H (CDCl₃): 7.65 - 7.05 (m, 9H); 3.82 (s, 2H); 3.76 (s, 3H); 2.52 (s, 3H).

b) Methyl α-[6-methyl-4-(3-phenylphenoxy)-5-pyrimidinyl]-acetate

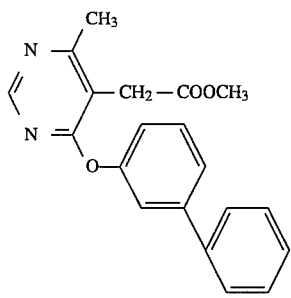

Methyl α-[6-methyl-2-chloro-4-(3-phenylphenoxy)-5-pyrimidinyl]-acetate is dissolved in methanol/triethylamine (50 ml/10 ml) and hydrogenated over Pd on charcoal (0.2 g). The reaction mixture is evaporated. Addition of potassium carbonate, ether extraction and chromatography on silica gel gives pure methyl α-[ 6-methyl-4-(3-phenylphenoxy)-5-pyrimidinyl]-acetate.

$^1$H (CDCl$_3$): 8.58 (s, 1H); 7.65 - 7.05 (m, 9H); 3.86 (s, 2H); 3.77 (s, 3H); 2.55 (s 3H).

c) Methyl α-[2-methyl-4-(3-phenylphenoxy)-5-pyrimidinyl]-acetate (8 mmol) are dissolved in methyl formate (10 ml) and added to a suspension of NaH (0.6 g, 80% in oil, 20 mmol) in 1,2-dimethoxyethane at room temperature. After 16 hours methyl iodide (2.5 ml, 40 mmol) is added with cooling. After further 2 hurs the reaction mixture is diluted with ether and washed with brine. Drying and chromatography on silicagel (eluent: hexane/ethlyacetate 1:1) gives the

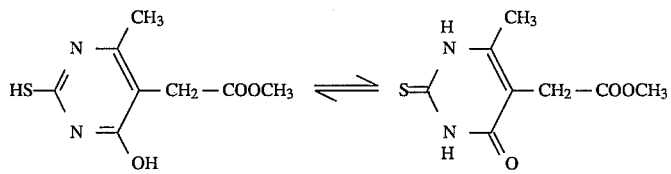

pure methyl α-[ 6-methyl-4-(3-phenylphenoxy)-5-pyrimidinyl]-β-methoxyacrylate as an oil.

EXAMPLE 3

Methyl α-[6-methyl,4-(3-phenylphenoxy)-5-pyrimidinyl]-β-methoxyacrylate

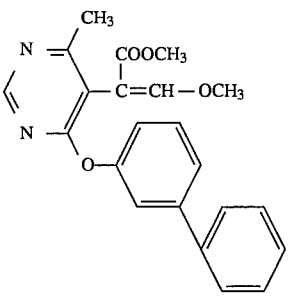

a) (4-Hydroxy-2-mercapto-6-methyl-5-pyrimidinyl)-acetic acid

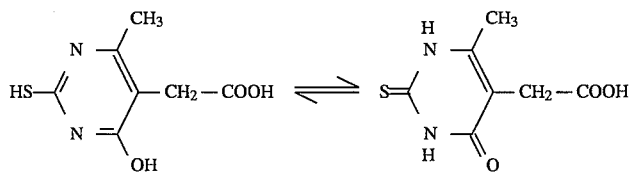

Thiourea (80 g, 1.05 mol) and dimethyl acetylsuccinate (188 g, 1.0 mol) are added at room temperature to a solution of sodium (46 g, 2.0 mol) in methanol (800 ml). The reaction mixture is refluxed for 14 hours. The crystalline precipitate is filtered and added with stirring to a concentrated aqueous solution of hydrochloric acid (250 ml). The resulting colorless crystalline precipitate is filtered, washed with methanol and dried at high vacuum to give 4-hydroxy-2-mercapto-6-methyl-5-pyrimidinyl acetic acid (190 g, 95%).

$^1$H-NMR (DMSO): 12.4 (s, 1H); 12.3 (s, 1H); 3.4 (s, 2H); 2.1 (s, 3H).

b) Methyl(4-hydroxy-2-mercapto-6-methyl-5-pyrimidinyl)-acetate

A solution of (4-hydroxy-2-mercapto-6-methyl-5-pyrimidinyl)-acetic acid (190 g, 0.95 mol) and concentrated sulfuric acid (50 ml) in methanol (1.51) is refluxed for 18 hours. The suspension is cooled and filtered to give methyl(4-hydroxy-2 -mercapto-6-methyl-5-pyrimidinyl)-acetate (160 g, 79%).

¹H-NMR (DMSO): 12.4 (s, 1H); 12.2 (s, 1H); 3.6 (s, 3H); 3.4 (s, 2H), 2.1 (s, 3H).

c) Methyl(4-hydroxy-6-methyl-5-pyrimidinyl)-acetate

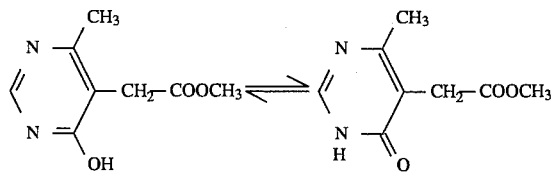

A suspension of methyl (4-hydroxy-2-mercapto-6-methyl-5-pyrimidinyl)-acetate (160 g, 0.75 mol) and Raney-Nickel in water (1.5 l) is refluxed for 16 hours. The reaction mixture is filtered and the filtrate concentrated under reduced pressure to 1/10 of the original volume. Filtration of the precipitate and drying gives methyl(4-hydroxy-6-methyl-5-pyrimidinyl)-acetate in form of colorless crystals (116 g, 85%).

¹H-NMR (DMSO): 12.4 (s, 1H); 8.0 (s, 1H); 3.6 (s, 3H); 3.4 (s, 2H); 2.1 (s, 3H).

d) Methyl (4-chloro-6-methyl-5-pyrimidinyl)-acetate

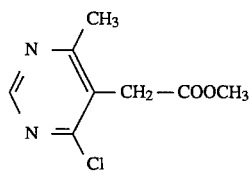

A suspension of methyl (4-hydroxy-6-methyl-5-pyrimidinyl)-acetate (116 g, 0.64 mol) in toluene (200 ml) and phosphorous oxychloride (94 ml, 1.0 mol) is refluxed for three hours. The solvent is removed under reduced pressure and the resulting oil is poured onto crushed ice with stirring. The pH is adjusted to 9 by adding potassium carbonate. Extraction with ether, drying and destillation under high vacuum gives methyl(4-chloro-6-methyl-5-pyrimidinyl)-acetate as a yellowish oil (105 g, 82%). b.p./1 torr 88°–91° C.

e) Methyl [6-methyl-4-(3-phenylphenoxy)-5-pyrimidinyl]-acetate

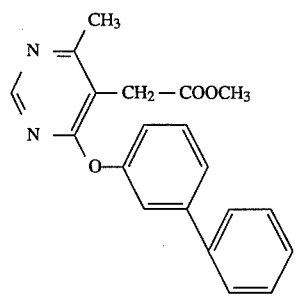

Methyl α-(4-chloro-6-methyl-5-pyrimidinyl)-acetate (130 g, 0.65 mol), m-hydroxybiphenyl (111 g, 0.65 mol) and potassium carbonate (179 g, 1.3 mol) in dimethylformamide (150 ml) are stirred at 110° C. for 1 hour. Water is added (300 ml) and the crystalline product is filtered and dried to give 175 g (81%) of methyl [6-methyl-4-(3-phenylphenoxy)-5-pyrimidinyl]-acetate having a m.p. of 113°–115° C.

f) Methyl α-[6-methyl-4-(3-phenylphenoxy)-5-pyrimidinyl]-β-dimethylamino acrylate

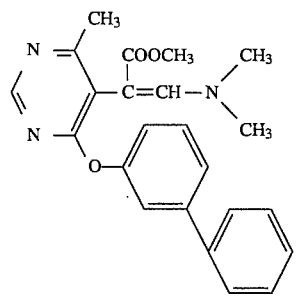

Methyl [6-methyl-4-(3-phenylphenoxy)-5-pyrimidinyl]-acetate (60 g, 0.18 mol) is added in one portion to a solution of t-BuOK (60 g, 0.53 mol) in 1,2-dimethoxyethane (0.5 l) at −40° C. After 1 hour dimethylformamide-dimethyl sulfate (1:1 adduct, 120 ml) is added at −50° C. The reaction mixture is allowed to warm to room temperature to give a yellow suspension. Addition of ether, washing repeatedly with brine and drying gives the crude methyl α-[4-methyl-6-(3-phenylphenoxy)-5-pyrimidinyl]-β-dimethylaminoacrylate (67 g, 95%) as an oil.

¹H-NMR (CDCl₃): 8.58 (s, 1H); 7.73 (s, 1H); 7.62-7.03 (m, 9H); 3.68 (s, 3H); 2.87 (s, 6H); 2.44 (s, 3H).

g) Methyl α-[6-methyl-4-(3-phenylphenoxy)-5-pyrimidinyl]-β-dimethylaminoacrylate (60 g, 0.15 mol) is dissolved in diethylether (300 ml) and a solution of p-toluene sulfonic acid (44 g, 0.23 mol) in water (200 ml) is added at room temperature with stirring. After 16 hours the mixture is partially neutralized by adding solid potassium bicarbonate (28 g). Extraction of the product with diethylether, drying of the organic phase (MgSO₄) and evaporation of the solvent gives the crude enol (52 g, 93%). The product is dissolved in dimethylformamide (100 ml) and potassium carbonate (33 g, 0.24 mol) and dimethyl sulfate (18.9 g, 0.15 mol) is added with cooling. After stirring the reaction mixture at room temperature for 3 hours, diethylether is added and the mixture is washed repeatedly with bring. Drying and chromatography on silicagel (eluant: hexane/ethyl acetate 1:1) gives the pure methyl α-[6-methyl-4(3-phenylphenoxy)-5-pyrimidinyl]-β-methoxyacrylate as a yellowish oil (46 g, 85%).

¹H-NMR (CDCl₃): 8.60 (s, 1H); 7.66 (s, 1H); 7.60-7.02 (m, 9H); 3.92 (s, 3H); 2.42 (s, 3H).

EXAMPLE 4

Methyl (4-chloro-2.6-dimethyl-5-pyrimidinyl)-acetate

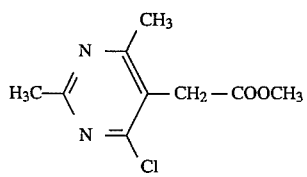

a) (2,6-Dimethyl-4-hydroxy-5-pyrimidinyl)-acetic acid

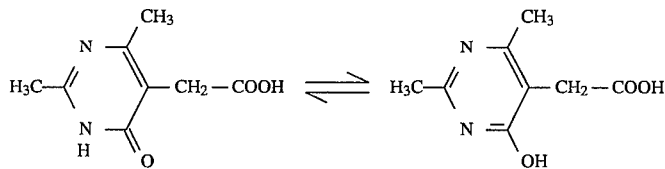

Dimethyl acetylsuccinate (188 g, 1 mol) is dissolved in sodiummethylate/methanol (1.1 mol in 500 ml) and added within 30 minutes to a solution of acetamidine hydrochloride (104 g, 1.1 mol) at 60° C. with stirring. After refluxing the mixture for 14 hours, the precipitated salt is removed by filtration and the filtrate is evaporated to dryness under reduced pressure. The resulting solid is suspended in acetone, filtered and dried to give (2,6-dimethyl-4-hydroxy-5-pyrimidinyl) acetic acid crystalline product (170 g, 93%).

$^1$H-NMR (DMSO): 12.3 (s, 1H); 3.2 (s, 2H); 2.2 (s, 3H); 2.1 (s, 3H).

b) Methyl (4-hydroxy-2,6-dimethyl-5-pyrimidinyl)-acetate for 16 hours. The volume of the reaction mixture is reduced to about 250 ml by evaporating the solvent under reduced pressure. Filtration and evaporation of the filtrate gives methyl (4-hydroxy-2,6-dimethyl-5-pyrimidinyl)-acetate (115 g, 63% as a colorless crystalline solid.

$^1$H-NMR (DMSO): 12.3 (s, 1H); 3.7 (s, 3H); 3.6 (s, 2H); 2.6 (s, 3H); 2.4 (s, 3H).

c) A suspension of methyl (4-hydroxy-2,6-dimethyl-5-pyri-

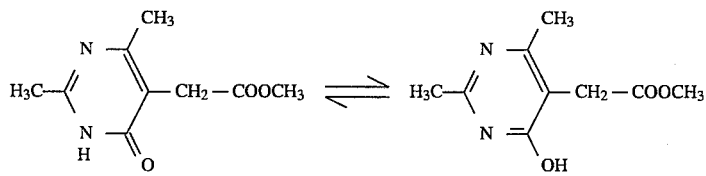

4-Hydroxy-2,6-dimethyl-5-pyrimidinyl)-acetic acid (170 g, 0.93 mol) is suspended in a saturated solution of hydrochloric acid in methanol (500 ml). The mixture is refluxed midinyl) acetate (0.64 mol) in toluene (200 ml) and phosphorous oxychloride (94 ml, 1.0 mol) is refluxed for three hours. The solvent is removed under reduced pressure and the resulting oil is poured onto crushed ice with stirring. The pH is adjusted to 9 by adding potassium carbonate. Extraction with ether, drying and destillation under high vacuum gives methyl (4-chloro-2,6-dimethyl-5-pyrimidinyl)-acetate as a solid with a m.p. of 53°– 54° C. in a yield of 80%.

EXAMPLE 5

Methyl (4-chloro-6-methyl-2-methylmercapto-5-pyrimidinyl)-acetate

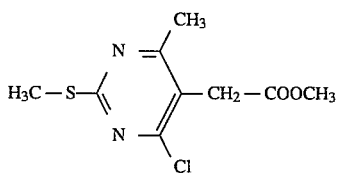

a) Methyl (4-hydroxy-6-methyl-2-methylmercapto-5-pyrimidinyl)-acetate

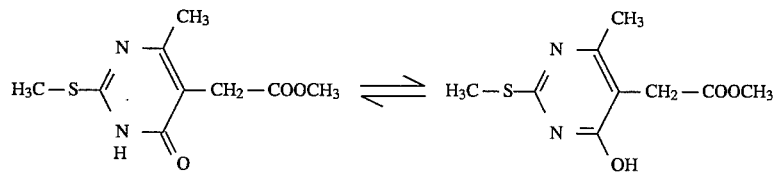

Methyl (4-hydroxy-6-methyl-2-mercapto-5-pyrimidinyl)-acetate (40 g, 0.19 mol) is dissolved in an aqueous solution of NaOH (8 g in 400 ml $H_2O$). Methyl iodide (29.5 g, 0.2 mol) is added and the mixture is stirred at room temperature for 4 hours. Filtration and drying at high vacuum gives methyl (4-hydroxy-6-methyl-2-methylmercapto-5-pyrimidinyl)-acetate (25.4 g, 60%) as a crystalline solid, having a m.p. of 200° C.

b) Methyl (4-hydroxy-6-methyl-2-methylmercapto-5-pyrimidinyl)-acetate (4.0 g, 17 mmol) is heated in a mixture of phosphoroxychloride (40 ml) and N,N-diethylaniline (5.5 ml) for 2 hours at 100° C. The excess phosphoroxychloride was removed by evaporation under vacuum and the residue poured into ice-water. Extraction with ethyl acetate, drying and filtration over silicagel gives methyl (4-chloro-6-methyl-2-methylmercapto-5-pyrimidinyl)-acetate as a crystalline solid (3.1 g, 72%), having a m.p. of 88° C.

The compounds of the following tables are obtained in analogous manner:

TABLE 1

[Structure: pyrimidine ring with R₁ substituent, COOCH₃ group, C=CH—OCH₃ side chain, and O—R₃ substituent]

| Comp. No. | R₁ | R₃ | physical data ¹H-NMR or/and m.p. |
|---|---|---|---|
| 1.01 | H | CH₃ | |
| 1.02 | CH₃ | CH₃ | 8.60 (s, 1H); 7.54 (s, 1H); 3.90 (s, 3H); 3.83 (s, 3H); 3.67 (s, 3H); 2.30 (s, 3H). (E-form) |
| 1.03 | CH₃ | 3-biphenylyl | 8.60 (s, 1H); 7.66 (s, 1H); 7.60–7.02 (m, 9H); 3.92 (s, 3H); 2.42 (s, 3H). (E-form) |
| 1.04 | H | 4-phenoxyphenyl | |
| 1.05 | H | 3-biphenylyl | 8.70 (s, 1H); 8.50 (s, 1H); 7.68 (s, 1H); 7.62–7.05 (m, 9H); 3.92 (s, 3H); 3.77 (s, 3H). (E-form) |
| 1.06 | H | β-naphthyl | |
| 1.07 | H | 3-trifluoromethylphenyl | 8.69 (s, 1H); 8.53 (s, 1H); 7.58 (s, 1H); 7.55–7.30 (m, 4H); 3.93 (s, 3H); 3.77 (s, 3H). (E-form) |
| 1.08 | CH₃ | 3-trifluoromethylphenyl | 8.60 (s, 1H); 7.67 (s, 1H); 7.53–7.27 (s, 4H); 3.92 (s, 3H); 3.74 (s, 3H); 2.42 (s, 3H). (E-form) |
| 1.09 | CH₃ | n-C₈H₁₇ | |
| 1.10 | CH₃ | 2,5-dimethylbenzyl | |
| 1.11 | CH₃ | 2-methylbenzyl | m.p. 119–120° C. (E-form) |
| 1.12 | CH₃ | 4-biphenylyl | |
| 1.13 | CH₃ | 3-phenoxyphenyl | 8.60 (s, 1H); 7.63 (s, 1H); 7.38–6.68 (m, 9H); 3.88 (s, 3H); 3.70 (s, 3H); 2.40 (s, 3H). (E-form) |
| 1.14 | CH₃ | 3-chlorophenyl | |
| 1.15 | CH₃ | 2,5-dimethylphenyl | |
| 1.16 | CH₃ | 2-phenoxyethyl | |
| 1.17 | CH₃ | 2-(3-trifluoromethylphenoxy)ethyl | |
| 1.18 | CH₃ | 2-(2,5-dimethyl-benzyloxy)ethyl | |
| 1.19 | CH₃ | 2-(3-methylbenzyloxy)ethyl | |
| 1.20 | CH₃ | 2-(4-biphenyloxy) ethyl | |
| 1.21 | CH₃ | 2-(3-phenoxy-phenoxy)ethyl | |
| 1.22 | CH₃ | 2-(3-chlorophenoxy)ethyl | |
| 1.23 | CH₃ | 2-(2,5-dimethyl-phenoxy)ethyl | |
| 1.24 | H | 3-trifluoromethoxypheny) | |
| 1.25 | H | n-C₈H₁₇ | |
| 1.26 | H | 2,5-dimethyl-benzyl | |
| 1.27 | H | 2-methylbenzyl | |
| 1.28 | H | 4-biphenylyl | |
| 1.29 | H | 3-phenoxyphenyl | |
| 1.30 | H | 3-chlorophenyl | |
| 1.31 | H | 2,5-dimethyl-phenyl | |
| 1.32 | H | 2-phenoxyethyl | |
| 1.33 | H | 2-(3-trifluoromethylphenoxy)ethyl | |
| 1.34 | H | 2-(2,5-dimethyl-benzyloxy)ethyl | |
| 1.35 | H | 2-(3-methyl-benzyloxy)ethyl | |
| 1.36 | H | 2-(4-biphenyloxy)ethyl | |
| 1.37 | H | 2-(3-phenoxy-phenoxy)ethyl | |
| 1.38 | H | 2-(3-chloro-phenoxy)ethyl | |
| 1.39 | H | 2-(2,5-dimethyl-phenoxy)ethyl | |
| 1.40 | CF₃ | CH₃ | |
| 1.41 | CF₃ | 3-biphenyiyl | |
| 1.42 | CH₃ | CH₂CF₃ | |
| 1.44 | CH₃ | 3-pyridylmethyl | |
| 1.45 | CH₃ | 3-tert.butylphenyl | m.p. 108–109° C. (E-form) |
| 1.46 | CH₃ | 3-methylphenyl | 8.58 (s, 1H); 7.63 (s, 1H); 7.32–6.85 (m, 4H); 3.92 (s, 3H); 3.73 (s, 3H); 2.40 (s, 3H); 2.37 (s, 3H). (E-form) |

TABLE 1-continued

Structure: pyrimidine with $R_1$, COOCH$_3$, C=CH—OCH$_3$, and O—$R_3$ substituents

| Comp. No. | $R_1$ | $R_3$ | physical data $^1$H-NMR or/and m.p. |
|---|---|---|---|
| 1.47 | CH$_3$ | 4-(C(CH$_3$)=N—OCH$_3$)-phenyl | m.p. 106–108° C. (E-form) |
| 1.48 | CH$_3$ | 3-methyl-5-isopropylphenyl | m.p. 111–112° C. (E-form) |
| 1.49 | CH$_3$ | 3-methyl-5-isopropylphenyl | m.p. 110–112° C. (Z-form) |
| 1.50 | CH$_3$ | 4-(C(CH$_3$)=N—O-allyl)-phenyl | m.p. 98–100° C. (E-form) |
| 1.51 | CH$_3$ | 3-(2-chloro-6-pyridyloxy)-phenyl | 8.61 (s, 1H); 7.65 (s, 1H); 7.68–6.78 (m, 7H); 3.90 (s, 3H); 3.73 (s, 3H); 2.40 (s, 3H). (E-form) |
| 1.52 | H | 4-chlorobenzyl | (E-form) |
| 1.53 | H | 4-chlorobenzyl | (Z-form) |
| 1.54 | CH$_3$ | 2,4-dichlorobenzyl | 130–132° C. (E-form) |
| 1.55 | CH$_3$ | 3-trifluoromethylbenzyl | 8.61 (s, 1H); 7.58 (s, 1H); 7.60–7.42 (m, 4H); 5.48 (s, 2H); 3.84 (s, 3H); 3.66 (s, 3H); 2.35 (s, 3H). (E-form) |
| 1.56 | CH$_3$ | 3-phenoxybenzyl | 8.60 (s, 1H); 7.52 (s, 1H); 7.38–6.88 (m, 9H); 5.40 (s, 2H); 3.78 (s, 3H); 3.63 (s, 3H); 2.33 (s, 3H). (E-form) |
| 1.57 | CH$_3$ | 2,5-dichlorobenzyl | m.p. 113–114° C. (E-form) |
| 1.58 | CH$_3$ | 3-(2-cyanophenoxy)-phenyl | m.p. 95–100° C. (E-form) |
| 1.59 | CH$_3$ | 3-isopropylphenyl | m.p. 87–89° C. (E-form) |
| 1.60 | CH$_3$ | 2,5-dichlorophenyl | m.p. 117° C. (E-form) |
| 1.61 | CH$_3$ | phenyl | |
| 1.62 | CH$_3$ | 3-(3-chloro-6-pyridazinyloxy)-phenyl | |
| 1.63 | CH$_3$ | 3-(4-quinazolinyloxy)-phenyl | |
| 1.64 | CH$_3$ | 3-(5-nitro-2-pyridyloxy)-phenyl | |
| 1.65 | CH$_3$ | 3-(2-nitrophenoxy)-phenyl | |
| 1.66 | CH$_3$ | 3-(3-nitro-2-pyridyloxy)-phenyl | |
| 1.67 | CH$_3$ | 3-(4-chloro-6-pyrimidinyloxy)-phenyl | |
| 1.68 | CH$_3$ | 3-(2-pyrimidinyloxy)-phenyl | |
| 1.69 | CH$_3$ | 3-(3,5-dimethylphenoxy)-phenyl | |
| 1.70 | CH$_3$ | 3-(2-chloro-4-methylphenoxy)-phenyl | |
| 1.71 | CH$_3$ | 3-(4-chloro-2-methylphenoxy)-phenyl | |
| 1.72 | CH$_3$ | 3-(3-cyanophenoxy)-phenyl | |
| 1.73 | CH$_3$ | 3-(4-cyanophenoxy)-phenyl | |
| 1.74 | CH$_3$ | 3-(2-trifluoromethylphenoxy)-phenyl | |
| 1.75 | CH$_3$ | 3-(3-trifluoromethylphenoxy)-phenyl | |
| 1.76 | CH$_3$ | 3-(4-trifluoromethylphenoxy)-phenyl | |
| 1.77 | CH$_3$ | 3-(4-(C(CH$_3$)=N—OCH$_3$)-phenoxy)-phenyl | |

TABLE 1-continued

[Structure: pyrimidine ring with R₁, COOCH₃, C=CH—OCH₃, and O—R₃ substituents]

| Comp. No. | R₁ | R₃ | physical data ¹H-NMR or/and m.p. |
|---|---|---|---|
| 1.78 | CH₃ | [structure: 4-methylphenyl-O-phenyl-C(CH₃)=N—OCH₃] | |
| 1.79 | CH₃ | 3-(3-chlorophenoxy)-phenyl | |
| 1.80 | CH₃ | 3-(4-chlorophenoxy)-phenyl | |
| 1.81 | CH₃ | 3-(3-methoxyphenoxy)-phenyl | |
| 1.82 | CH₃ | 3-(2-methylphenoxy)-phenyl | |
| 1.83 | CH₃ | 3-(2,5-dimethylphenoxy)-phenyl | |
| 1.84 | CH₃ | 3-(2,3-dimethylphenoxy)-phenyl | |
| 1.85 | CH₃ | 3-(3-methylphenoxy)-phenyl | |
| 1.86 | CH₃ | 3-benzyloxy-phenyl | |
| 1.87 | CH₃ | 3-(2-methylbenzyloxy)-phenyl | 8.60 (s, 1H); 7.63 (s, 1H); 7.42–6.68 (m, 8H); 5.02 (s, 3H); 3.90 (s, 2H); 3.73 (s, 3H); 2.42 (s, 3H); 2.37 (s, 3H). (E-form) |
| 1.88 | CH₃ | 3-(2-chlorobenzyloxy)-phenyl | 8.6 (s, 1H); 7.6 (s, 1H); 7.6–6–65 (m, 9H); 5.15 (s, 2H); 3.9 (s, 3H); 3.7 (s, 3H); 2.40 (s, 3H). (E-form) |
| 1.89 | CH₃ | 3-(2,5-dichlorobenzyloxy)-phenyl | |
| 1.90 | CH₃ | 3-(2,5-dimethylbenzyloxy)-phenyl | 8.6 (s, 1H); 7.6 (s, 1H); 7.3–6.5 (m, 9H); 4.95 (s, 2H); 3.9 (s, 3H); 3.7 (s, 3H); 2.4 (s, 3H); 2.3 (2xs, 6H). (E-form) |
| 1.91 | CH₃ | 3-(3-chlorobenzyloxy)-phenyl | 8.6 (s, 1H); 7.6 (s, 1H); 7.4–6.6 (m, 9H); 5.0 (s, 2H); 3.9 (s, 3H); 3.7 (s, 3H); 2.4 (s, 3H). (E-form) |
| 1.92 | CH₃ | 3-(3-methylbenzyloxy)-phenyl | |
| 1.93 | CH₃ | 3-(4-chlorobenzyloxy)-phenyl | 8.6 (s, 1H); 7.6 (s, 1H); 7.35–6.6 (m, 9H); 5.0 (s, 2H); 3.9 (s, 3H); 3.7 (s, 3H); 2.4 (s, 3H). (E-form) |
| 1.94 | CH₃ | 3-(3,4-dichlorobenzyloxy)-phenyl | |
| 1.95 | CH₃ | 3-(3-chloro-4-methylbenzyloxy)-phenyl | |
| 1.96 | CH₃ | 3-(2,6-dichlorobenzyloxy)-phenyl | |
| 1.97 | CH₃ | 3-(2,4-dichlorobenzyloxy)-phenyl | |
| 1.98 | CH₃ | 3-(2,3-dichlorobenzyloxy)-phenyl | |
| 1.99 | CH₃ | 3-(3-methoxybenzyloxy)-phenyl | |
| 1.100 | CH₃ | [structure: 4-methylphenyl-O-CH₂-benzodioxole] | |
| 1.101 | CH₃ | 3-(2-cyanobenzyloxy)-phenyl | |
| 1.102 | CH₃ | 3-(4-nitrobenzyloxy)-phenyl | |
| 1.103 | CH₃ | 3-(2-nitrobenzyloxy)-phenyl | |
| 1.104 | CH₃ | 3-(phenylethoxy)-phenyl | |
| 1.105 | CH₃ | 3-(phenoxy-methyl)-phenyl | |
| 1.106 | CH₃ | 3-(3-chlorophenoxymethyl)-phenyl | |

TABLE 1-continued
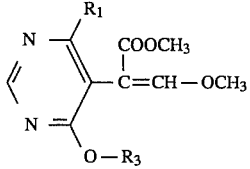
| Comp. No. | R₁ | R₃ | physical data $^1$H-NMR or/and m.p. |
|---|---|---|---|
| 1.107 | CH₃ | 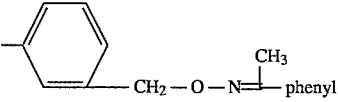 | |
| 1.108 | CH₃ | 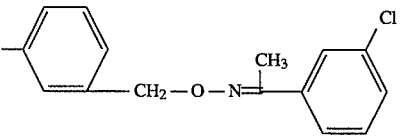 | |
| 1.109 | CH₃ | 3-(2,5-dimethylphenoxy-methyl)-phenyl | |
| 1.110 | CH₃ | 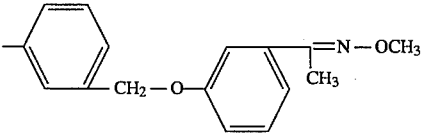 | |
| 1.111 | CH₃ | 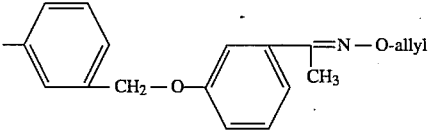 | |
| 1.112 | CH₃ | 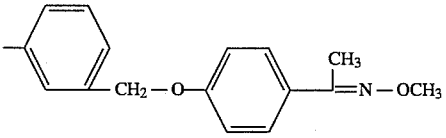 | |
| 1.113 | CH₃ | 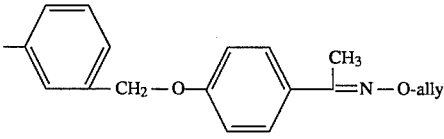 | |
| 1.114 | CH₃ | 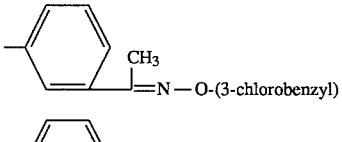 | |
| 1.115 | CH₃ | 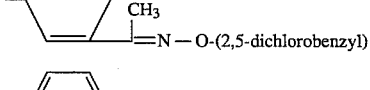 | |
| 1.116 | CH₃ | 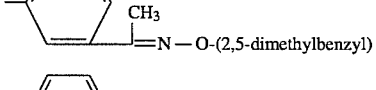 | |
| 1.117 | CH₃ | 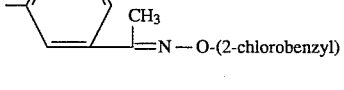 | |

TABLE 1-continued

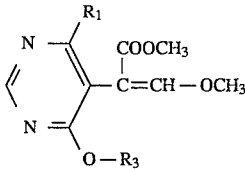

| Comp. No. | R₁ | R₃ | physical data ¹H-NMR or/and m.p. |
|---|---|---|---|
| 1.118 | CH₃ | [phenyl-C(CH₃)=N—O-(4-nitrobenzyl)] | |
| 1.119 | CH₃ | [phenyl-C(CH₃)=N—O-(2-nitrobenzyl)] | |
| 1.120 | CH₃ | [phenyl-C(CH₃)=N—O-(3,4-dichlorobenzyl)] | |
| 1.121 | CH₃ | [phenyl-C(CH₃)=N—O-(2,4-dichlorobenzyl)] | |
| 1.122 | CH₃ | [phenyl-C(CH₃)=N—O-benzyl] | 8.58 (s, 1H); 7.64 (s, 1H); 7.53–7.03(m, 9H); 5.22 (s, 2H); 3.90 (s, 3H); 3.72 (s, 3H); 2.41 (s, 3H); 2.25 (s,3H). |
| 1.123 | CH₃ | [phenyl-O-CH(CH₃)-(4-chlorophenyl)] | |
| 1.124 | CH₃ | [phenyl-CH(CH₃)-O-(4-chlorophenyl)] | |
| 1.125 | CH₃ | 3-(3-thienyl)-phenyl | |
| 1.126 | CH₃ | 3-(2-naphthyl)-phenyl | |
| 1.127 | CH₃ | 3-(4-phenyl)-phenyl | |
| 1.128 | CH₃ | 3-(2-pyridyl)-phenyl | |

TABLE 2

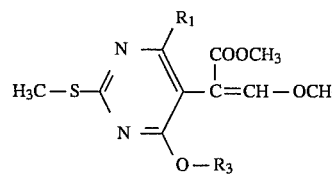

| Comp. No. | R₁ | R₃ | physical data ¹H-NMR or/and m.p. |
|---|---|---|---|
| 2.01 | H | CH₃ | |
| 2.02 | CH₃ | CH₃ | |
| 2.03 | CH₃ | 3-biphenylyl | 7.62 (s, 1H); 7.60–7.03 (m, 9H); |

TABLE 2-continued

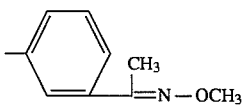

| Comp. No. | R₁ | R₃ | physical data ¹H-NMR or/and m.p. |
|---|---|---|---|
| | | | 3.90 (s, 3H); 3.74 (s, 3H); 2.32 (s, 3H); 2.30 (s, 3H). (E-form) |
| 2.04 | H | 4-phenoxyphenyl | |
| 2.05 | H | 3-biphenylyl | |
| 2.06 | H | β-naphthyl | |
| 2.07 | H | 3-trifluoromethylphenyl | |
| 2.08 | CH₃ | 3-trifluoromethylphenyl | |
| 2.09 | CH₃ | n-C₈H₁₇ | |
| 2.10 | CH₃ | 2,5-dimethylbenzyl | |
| 2.11 | CH₃ | 2-methylbenzyl | |
| 2.12 | CH₃ | 4-biphenylyl | |
| 2.13 | CH₃ | 3-phenoxyphenyl | |
| 2.14 | CH₃ | 3-chlorophenyl | |
| 2.15 | CH₃ | 2,5-dimethylphenyl | |
| 2.16 | CH₃ | 2-phenoxyethyl | |
| 2.17 | CH₃ | 2-(3-trifluoromethylphenoxy)ethyl | |
| 2.18 | CH₃ | 2-(2,5-dimethyl-benzyloxy)ethyl | |
| 2.19 | CH₃ | 2-(3-methylbenzyloxy)ethyl | |
| 2.20 | CH₃ | 2-(4-biphenyloxy) ethyl | |
| 2.21 | CH₃ | 2-(3-phenoxy-phenoxy)ethyl | |
| 2.22 | CH₃ | 2-(3-chlorophenoxy)ethyl | |
| 2.23 | CH₃ | 2-(2,5-dimethyl-phenoxy)ethyl | |
| 2.24 | H | 3-trifluoromethoxyphenyl | |
| 2.25 | H | n-C₈H₁₇ | |
| 2.26 | H | 2,5-dimethyl-benzyl | |
| 2.27 | H | 2-methylbenzyl | |
| 2.28 | H | 4-biphenylyl | |
| 2.29 | H | 3-phenoxyphenyl | |
| 3.30 | H | 3-chlorophenyl | |
| 2.31 | H | 2,5-dimethyl-phenyl | |
| 2.32 | H | 2-phenoxyethyl | |
| 2.33 | H | 2-(3-trifluoromethylphenoxy)ethyl | |
| 2.34 | H | 2-(2,5-dimethyl-benzyloxy)ethyl | |
| 2.35 | H | 2-(3-methyl-benzyloxy)ethyl | |
| 2.36 | H | 2-(4-biphenyloxy)ethyl | |
| 2.37 | H | 2-(3-phenoxy-phenoxy)ethyl | |
| 2.38 | H | 2-(3-chloro-phenoxy)ethyl | |
| 2.39 | H | 2-(2,5-dimethyl-phenoxy)ethyl | |
| 2.40 | CF₃ | CH₃ | |
| 2.41 | CF₃ | 3-biphenylyl | |
| 2.42 | CH₃ | CH₂CF₃ | |
| 2.43 | CH₃ | furfuryl | |
| 2.44 | CH₃ | 3-pyridylmethyl | |
| 2.45 | CH₃ | 3-tert.butylphenyl | 7.62 (s, 1H); 7.31–6.85 (m, 4H); 3.90 (s, 3H); 3.73 (s, 3H); 2.32 (s, 3H); 2.22 (s, 3H); 1.30 (s, 9H). (E-form) |
| 2.46 | CH₃ | 3-methylphenyl | |
| 2.47 | CH₃ | ![structure: phenyl with CH₃ and =N—OCH₃] | |
| 2.48 | CH₃ | 3-methyl-5-isopropylphenyl | 7.60 (s, 1H); 6.85 (s, 1H); 6.76 (s, 1H); 6.72 (s, 1H); 3.89 (s, 3H); 3.72 (s, 3H); 2.82 (dxg, 1H); 2.32 (2xs, 6H); 2.26 (s, 3H); 1.22 (d, 6H) (E-form) |
| 2.49 | CH₃ | 3-methyl-5-isopropylphenyl | |

TABLE 2-continued

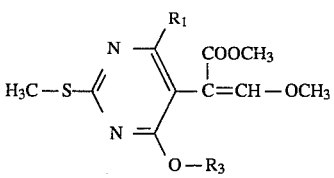

| Comp. No. | R₁ | R₃ | physical data ¹H-NMR or/and m.p. |
|---|---|---|---|
| 2.50 | CH₃ | 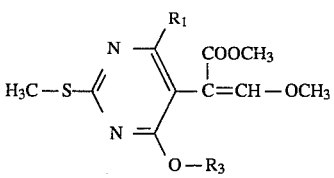 | |
| 2.51 | CH₃ | 3-(2-chloro-6-pyridyloxy)-phenyl | |
| 2.52 | H | 4-chlorobenzyl | |
| 2.53 | H | 4-chlorobenzyl | |
| 2.54 | CH₃ | 2,4-dichlorobenzyl | |
| 2.55 | CH₃ | 3-trifluoromethylbenzyl | |
| 2.56 | CH₃ | 3-phenoxybenzyl | |
| 2.57 | CH₃ | 2,5-dichlorobenzyl | |
| 2.58 | CH₃ | 3-(2-cyanophenoxy)-phenyl | 7.62 (s, 1H); 7.68–7.85 (m, 8H); 3.89 (s, 3H); 3.70 (s, 3H); 2.32 (2xs, 6H). (E-form) |
| 2.59 | CH₃ | 3-isopropylphenyl | |
| 2.60 | CH₃ | 2,5-dichlorophenyl | |
| 2.61 | CH₃ | phenyl | |
| 2.62 | CH₃ | 3-(3-chloro-6-pyridazinyl-oxy)-phenyl | |
| 2.63 | CH₃ | 3-(4-quinazolinyloxy)-phenyl | |
| 2.64 | CH₃ | 3-(5-nitro-2-pyridyloxy)-phenyl | |
| 2.65 | CH₃ | 3-(2-nitrophenoxy)-phenyl | |
| 2.66 | CH₃ | 3-(3-nitro-2-pyridyloxy)-phenyl | |
| 2.67 | CH₃ | 3-(4-chloro-6-pyrimidinyloxy)-phenyl | |
| 2.68 | CH₃ | 3-(2-pyrimidinyloxy)-phenyl | |
| 2.69 | CH₃ | 3-(3,5-dimethylphenoxy)-phenyl | |
| 2.70 | CH₃ | 3-(2-chloro-4-methylphenoxy)-phenyl | |
| 2.71 | CH₃ | 3-(4-chloro-2-methylphenoxy)-phenyl | |
| 2.72 | CH₃ | 3-(3-cyanophenoxy)-phenyl | |
| 2.73 | CH₃ | 3-(4-cyanophenoxy)-phenyl | 7.62 (s, 1H); 7.65–6.83 (m, 8H); 3.89 (s, 3H); 3.72 (s, 3H); 2.32 (2xs, 6H). (E-form) |
| 2.74 | CH₃ | 3-(2-trifluoromethyl-phenoxy)-phenyl | |
| 2.75 | CH₃ | 3-(3-trifluoromethyl-phenoxy)-phenyl | 7.60 (s, 1H); 7.50–6.78 (m, 8H); 3.87 (s, 3H), 3.70 (s, 3H); 2.32 (s, 3H); 2.30 (s, 3H). (E-form) |
| 2.76 | CH₃ | 3-(4-trifluoromethyl-phenoxy)-phenyl | |
| 2.77 | CH₃ | 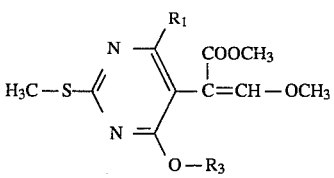 | |
| 2.78 | CH₃ | 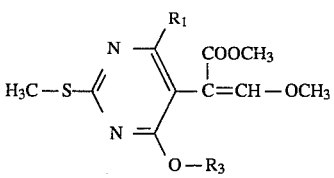 | |
| 2.79 | CH₃ | 3-(3-chlorophenoxy)-phenyl | |
| 2.80 | CH₃ | 3-(4-chlorophenoxy)-phenyl | |
| 2.81 | CH₃ | 3-(3-methoxyphenoxy)- | |

TABLE 2-continued

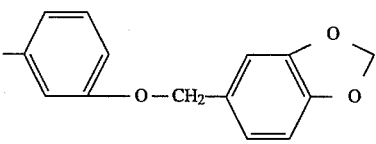

| Comp. No. | R₁ | R₃ | physical data ¹H-NMR or/and m.p. |
|---|---|---|---|
| 2.82 | CH₃ | 3-(2-methylphenoxy)-phenyl | |
| 2.83 | CH₃ | 3-(2,5-dimethylphenoxy)-phenyl | |
| 2.84 | CH₃ | 3-(2,3-dimethylphenoxy)-phenyl | |
| 2.85 | CH₃ | 3-(3-methylphenoxy)-phenyl | |
| 2.86 | CH₃ | 3-benzyloxy-phenyl | |
| 2.87 | CH₃ | 3-(2-methylbenzyloxy)-phenyl | |
| 2.88 | CH₃ | 3-(2-chlorobenzyloxy)-phenyl | 7.61 (s, 1H); 7.59–6.70 (m, 8H); 5.15 (s, 2H); 3.89 (s, 3H); 3.72 (s, 3H); 2.32 (s, 3H); 2.30 (s, 3H). (E-form) |
| 2.89 | CH₃ | 3-(2,5-dichlorobenzyloxy)-phenyl | |
| 2.90 | CH₃ | 3-(2,5-dimethylbenzyloxy)-phenyl | 7.61 (s, 1H); 7.30–6.71 (m, 7H); 4.97 (s, 2H); 3.88 (s, 3H); 3.72 (s, 3H); 2.32 (2xs, 6H); 2.28 (s, 3H). (E-form) |
| 2.91 | CH₃ | 3-(3-chlorobenzyloxy)-phenyl | 7.61 (s, 1H); 7.42–6.68 (m, 8H); 5.02 (s, 2H); 3.88 (s, 3H); 3.71 (s, 3H); 2.32 (s, 3H); 2.28 (s, 3H). (E-form) |
| 2.92 | CH₃ | 3-(3-methylbenzyloxy)-phenyl | |
| 2.93 | CH₃ | 3-(4-chlorobenzyloxy)-phenyl | 7.62 (s, 1H); 7.38–6.70 (s, 8H); 5.02 (s, 2H); 3.88 (s, 3H); 3.72 (s, 3H); 2.32 (s, 3H); 2.28 (s, 3H). (E-form) |
| 2.94 | CH₃ | 3-(3,4-dichlorobenzyloxy)-phenyl | |
| 2.95 | CH₃ | 3-(3-chloro-4-methylbenzyloxy)-phenyl | |
| 2.96 | CH₃ | 3-(2,6-dichlorobenzyloxy)-phenyl | |
| 2.97 | CH₃ | 3-(2,4-dichlorobenzyloxy)-phenyl | |
| 2.98 | CH₃ | 3-(2,3-dichlorobenzyloxy)-phenyl | |
| 2.99 | CH₃ | 3-(3-methoxybenzyloxy)-phenyl | |
| 2.100 | CH₃ | 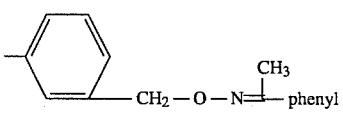 | |
| 2.101 | CH₃ | 3-(2-cyanobenzyloxy)-phenyl | |
| 2.102 | CH₃ | 3-(4-nitrobenzyloxy)-phenyl | |
| 2.103 | CH₃ | 3-(2-nitrobenzyloxy)-phenyl | |
| 2.104 | CH₃ | 3-(phenylethoxy)-phenyl | 7.60 (s, 1H); 7.36–6.65 (m, 9H); 4.15 (L, 2H); 3.88 (s, 3H); 3.72 (s, 3H); 3.07 (t, 2H); 2.31 (s, 3H); 2.25 (s, 3H). (E-form) |
| 2.105 | CH₃ | 3-(phenoxy-methyl)-phenyl | |
| 2.106 | CH₃ | 3-(3-chlorophenoxymethyl)-phenyl | |
| 2.107 | CH₃ | [phenyl–CH₂–O–N=C(CH₃)–phenyl] | |

TABLE 2-continued

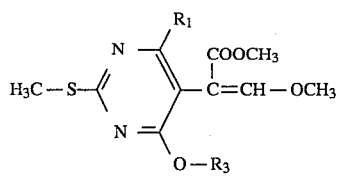

| Comp. No. | R₁ | R₃ | physical data ¹H-NMR or/and m.p. |
|---|---|---|---|
| 2.108 | CH₃ | 4-[[(1-(3-chlorophenyl)ethylidene)amino]oxymethyl]phenyl | |
| 2.109 | CH₃ | 3-(2,5-dimethylphenoxymethyl)-phenyl | |
| 2.110 | CH₃ | 4-[[3-(1-(methoxyimino)ethyl)phenoxy]methyl]phenyl | |
| 2.111 | CH₃ | 4-[[3-(1-(allyloxyimino)ethyl)phenoxy]methyl]phenyl | |
| 2.112 | CH₃ | 4-[[4-(1-(methoxyimino)ethyl)phenoxy]methyl]phenyl | |
| 2.113 | CH₃ | 4-[[4-(1-(allyloxyimino)ethyl)phenoxy]methyl]phenyl | |
| 2.114 | CH₃ | 4-[1-[(3-chlorobenzyl)oxyimino]ethyl]phenyl | |
| 2.115 | CH₃ | 4-[1-[(2,5-dichlorobenzyl)oxyimino]ethyl]phenyl | |
| 2.116 | CH₃ | 4-[1-[(2,5-dimethylbenzyl)oxyimino]ethyl]phenyl | |
| 2.117 | CH₃ | 4-[1-[(2-chlorobenzyl)oxyimino]ethyl]phenyl | |
| 2.118 | CH₃ | 4-[1-[(4-nitrobenzyl)oxyimino]ethyl]phenyl | |

TABLE 2-continued $$H_3C-S-\underset{N}{\overset{N}{\bigcirc}}\underset{O-R_3}{\overset{R_1}{\bigcirc}}C=CH-OCH_3$$

| Comp. No. | R₁ | R₃ | physical data ¹H-NMR or/and m.p. |
|---|---|---|---|
| 2.119 | CH₃ | (4-methylphenyl)-C(CH₃)=N—O-(2-nitrobenzyl) | |
| 2.120 | CH₃ | (4-methylphenyl)-C(CH₃)=N—O-(3,4-dichlorobenzyl) | |
| 2.121 | CH₃ | (4-methylphenyl)-C(CH₃)=N—O-(2,4-dichlorobenzyl) | |
| 2.122 | CH₃ | (4-methylphenyl)-C(CH₃)=N—O-benzyl | |
| 2.123 | CH₃ | 4-[CH(CH₃)-(4-chlorophenyl)]-phenyl-O- | |
| 2.124 | CH₃ | 4-[CH(CH₃)-O-(4-chlorophenyl)]-phenyl- | |
| 2.125 | CH₃ | 3-(3-thienyl)-phenyl | |
| 2.126 | CH₃ | 3-(2-naphthyl)-phenyl | |
| 2.127 | CH₃ | 3-(4-phenyl)-phenyl | |
| 2.128 | CH₃ | 3-(2-pyridyl)-phenyl | |
| 2.129 | CH₃ | 3-(4-bromobenzyloxy)phenyl | 7.61 (s, 1H); 7.52–6.70 (s, 8H); 4.98 (2, 2H); 3.88 (s, 3H); 3.72 (s, 3H); 2.32 (s, 3H); 2.28 (s, 3H). (E-form) |

TABLE 3

$$H_3C-\underset{N}{\overset{N}{\bigcirc}}\underset{O-R_3}{\overset{R_1}{\bigcirc}}C=CH-OCH_3$$

| Comp. No. | R₁ | R₃ | physical data ¹H-NMR or/and m.p. |
|---|---|---|---|
| 3.01 | H | CH₃ | 8.18 (s, 1H); 7.57 (s, 1H); 3.95 (s, 3H); 3.84 (s, 3H); 3.70 (s, 3H); 2.62 (s, 3H). (E-form) |
| 3.02 | CH₃ | CH₃ | |
| 3.03 | CH₃ | 3-biphenylyl | 7.62 (s, 1H); 7.60–7.03 (m, 9H); 3.89 (s, 3H); 3.72 (s, 3H); 2.50 (s, 3H); 2.38 (s, 3H). (E-form) |

TABLE 3-continued

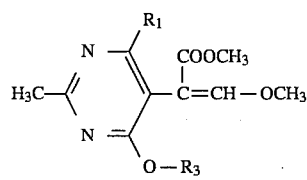

| Comp. No. | R₁ | R₃ | physical data ¹H-NMR or/and m.p. |
|---|---|---|---|
| 3.04 | H | 4-phenoxyphenyl | 8.36 (s, 1H); 7.64 (s, 1H); 7.40–6.97 (m, 9H); 3.90 (s, 3H); 3.75 (s, 3H); 2.53 (s, 3H). (E-form) |
| 3.05 | H | 3-biphenylyl | 8.38 (s, 1H); 7.63 (s, 1H); 7.62–7.05 (m, 9H); 3.90 (s, 3H); 3.74 (s, 3H); 2.53 (s, 3H). (E-form) |
| 3.06 | H | β-naphthyl | 8.39 (s, 1H); 7.88–7.75 (m, 3H); 7.65 (s, 1H); 7.57–7.22 (m, 4H); 3.92 (s, 3H); 3.74 (s, 3H); 2.49 (s, 3H); m.p. 108–110° C. (E-form) |
| 3.07 | H | 3-trifluoromethylphenyl | 8.38 (s, 1H); 7.62 (s, 1H); 7.50–7.25 (s, 4H); 3.87 (s, 3H); 3.71 (s, 3H); 2.50 (s, 3H); m.p. 100–102° C. (E-form) |
| 3.08 | CH₃ | 3-trifluoromethylphenyl | |
| 3.09 | CH₃ | n-C₈H₁₇ | |
| 3.10 | CH₃ | 2,5-dimethylbenzyl | |
| 3.11 | CH₃ | 2-methylbenzyl | |
| 2.12 | CH₃ | 4-biphenylyl | |
| 3.13 | CH₃ | 3-phenoxyphenyl | |
| 3.14 | CH₃ | 3-chlorophenyl | |
| 3.15 | CH₃ | 2,5-dimethylphenyl | |
| 3.16 | CH₃ | 2-phenoxyethyl | |
| 3.17 | CH₃ | 2-(3-trifluoromethylphenoxy)ethyl | |
| 3.18 | CH₃ | 2-(2,5-dimethyl-benzyloxy)ethyl | |
| 3.19 | CH₃ | 2-(3-methylbenzyloxy)ethyl | |
| 3.20 | CH₃ | 2-(4-biphenyloxy)ethyl | |
| 3.21 | CH₃ | 2-(3-phenoxy-phenoxy)ethyl | |
| 3.22 | CH₃ | 2-(3-chlorophenoxy)ethyl | |
| 3.23 | CH₃ | 2-(2,5-dimethyl-phenoxy)ethyl | |
| 3.24 | H | 3-trifluoromethoxyphenyl | |
| 3.25 | H | n-C₈H₁₇ | |
| 3.26 | H | 2,5-dimethyl-benzyl | |
| 3.27 | H | 2-methylbenzyl | |
| 3.28 | H | 4-biphenylyl | |
| 3.29 | H | 3-phenoxyphenyl | |
| 3.30 | H | 3-chlorophenyl | |
| 3.31 | H | 2,5-dimethyl-phenyl | |
| 3.32 | H | 2-phenoxyethyl | |
| 3.33 | H | 2-(3-trifluoromethylphenoxy)ethyl | |
| 3.34 | H | 2-(2,5-dimethyl-benzyloxy)ethyl | |
| 3.35 | H | 2-(3-methyl-benzyloxy)ethyl | |
| 3.36 | H | 2-(4-biphenyloxy)ethyl | |
| 3.37 | H | 2-(3-phenoxy- phenoxy)ethyl | |
| 3.38 | H | 2-(3-chloro-phenoxy)ethyl | |
| 3.39 | H | 2-(2,5-dimethyl-phenoxy)ethyl | |
| 3.40 | CF₃ | CH₃ | |
| 3.41 | CF₃ | 3-biphenylyl | |
| 3.42 | CH₃ | CH₂CF₃ | |
| 3.43 | CH₃ | furfuryl | |
| 3.44 | CH₃ | 3-pyridylmethyl | |
| 3.45 | CH₃ | 3-tert.butylphenyl | |
| 3.46 | CH₃ | 3-methylphenyl | |
| 3.47 | CH₃ | ![phenyl-C(CH₃)=N-OCH₃] | |
| 3.48 | CH₃ | 3-methyl-5-isopropylphenyl | 7.60 (s, 1H); 6.85 (s, 1H); 6.73 (s, |

TABLE 3-continued

[Structure: pyrimidine with H₃C- group, R₁, COOCH₃, C=CH-OCH₃, O-R₃]

| Comp. No. | R₁ | R₃ | physical data ¹H-NMR or/and m.p. |
|---|---|---|---|
| | | | 1H); 6.70 (s, 1H); 3.88 (s, 3H); 3.72 (s, 3H); 2.85 (dxq; 1H); 2.50 (s, 3H); 2.38 (s, 3H); 2.35 (s, 3H); 1.23 (d, 6H). (E-form). |
| 3.49 | CH₃ | 3-methyl-5-isopropylphenyl | (Z-form) |
| 3.50 | CH₃ | [phenyl-C(CH₃)=N-O-allyl] | |
| 3.51 | CH₃ | 3-(2-chloro-6-pyridyloxy)-phenyl | |
| 3.52 | H | 4-chlorobenzyl | 8.23 (s, 1H); 7.53 (s, 1H); 7.32 (s, 4H); 5.39 (s, 2H); 3.82 (s, 3H); 3.65 (s, 3H); 2.63 (s, 3H). (E-form) |
| 3.53 | H | 4-chlorobenzyl | m.p. 135–137° C. (Z-form) |
| 3.54 | CH₃ | 2,4-dichlorobenzyl | |
| 3.55 | CH₃ | 3-trifluoromethylbenzyl | |
| 3.56 | CH₃ | 3-phenoxybenzyl | |
| 3.57 | CH₃ | 2,5-dichlorobenzyl | |
| 3.58 | CH₃ | 3-(2-cyanophenoxy)-phenyl | |
| 3.59 | CH₃ | 3-isopropylphenyl | |
| 3.60 | CH₃ | 2,5-dichlorophenyl | |
| 3.61 | CH₃ | phenyl | |
| 3.62 | CH₃ | 3-(3-chloro-6-pyridazinyloxy)-phenyl | |
| 3.63 | CH₃ | 3-(4-quinazolinyloxy)-phenyl | |
| 3.64 | CH₃ | 3-(5-nitro-2-pyridyloxy)-phenyl | |
| 3.65 | CH₃ | 3-(2-nitrophenoxy)-phenyl | |
| 3.66 | CH₃ | 3-(3-nitro-2-pyridyloxy)-phenyl | |
| 3.67 | CH₃ | 3-(4-chloro-6-pyrimidinyloxy)-phenyl | |
| 3.68 | CH₃ | 3-(2-pyrimidinyloxy)-phenyl | |
| 3.69 | CH₃ | 3-(3,5-dimethylphenoxy)-phenyl | |
| 3.70 | CH₃ | 3-(2-chloro-4-methylphenoxy)-phenyl | |
| 3.71 | CH₃ | 3-(4-chloro-2-methylphenoxy)-phenyl | |
| 3.72 | CH₃ | 3-(3-cyanophenoxy)-phenyl | |
| 3.73 | CH₃ | 3-(4-cyanophenoxy)-phenyl | |
| 3.74 | CH₃ | 3-(2-trifluoromethylphenoxy)-phenyl | |
| 3.75 | CH₃ | 3-(3-trifluoromethylphenoxy)-phenyl | |
| 3.76 | CH₃ | 3-(4-trifluoromethylphenoxy)-phenyl | |
| 3.77 | CH₃ | [phenyl-O-phenyl-C(CH₃)=N-OCH₃] | |
| 3.78 | CH₃ | [phenyl-O-phenyl-C(CH₃)=N-OCH₃] | |

TABLE 3-continued $$\text{structure with } R_1, R_3, \text{COOCH}_3, \text{OCH}_3 \text{ substituents on pyrimidine core}$$

| Comp. No. | R₁ | R₃ | physical data ¹H-NMR or/and m.p. |
|---|---|---|---|
| 3.79 | CH₃ | 3-(3-chlorophenoxy)-phenyl | |
| 3.80 | CH₃ | 3-(4-chlorophenoxy)-phenyl | |
| 3.81 | CH₃ | 3-(3-methoxyphenoxy)-phenyl | |
| 3.82 | CH₃ | 3-(2-methylphenoxy)-phenyl | |
| 3.83 | CH₃ | 3-(2,5-dimethylphenoxy)-phenyl | |
| 3.84 | CH₃ | 3-(2,3-dimethylphenoxy)-phenyl | |
| 3.85 | CH₃ | 3-(3-methylphenoxy)-phenyl | |
| 3.86 | CH₃ | 3-benzyloxy-phenyl | |
| 3.87 | CH₃ | 3-(2-methylbenzyloxy)-phenyl | |
| 3.88 | CH₃ | 3-(2-chlorobenzyloxy)-phenyl | |
| 3.89 | CH₃ | 3-(2,5-dichlorobenzyloxy)-phenyl | |
| 3.90 | CH₃ | 3-(2,5-dimethylbenzyloxy)-phenyl | |
| 3.91 | CH₃ | 3-(3-chlorobenzyloxy)-phenyl | |
| 3.92 | CH₃ | 3-(3-methylbenzyloxy)-phenyl | |
| 3.93 | CH₃ | 3-(4-chlorobenzyloxy)-phenyl | |
| 3.94 | CH₃ | 3-(3,4-dichlorobenzyloxy)-phenyl | |
| 3.95 | CH₃ | 3-(3-chloro-4-methylbenzyloxy)-phenyl | |
| 3.96 | CH₃ | 3-(2,6-dichlorobenzyloxy)-phenyl | |
| 3.97 | CH₃ | 3-(2,4-dichlorobenzyloxy)-phenyl | |
| 3.98 | CH₃ | 3-(2,3-dichlorobenzyloxy)-phenyl | |
| 3.99 | CH₃ | 3-(3-methoxybenzyloxy)-phenyl | |
| 3.100 | CH₃ | phenyl-O-CH₂-(3,4-methylenedioxyphenyl) | |
| 3.101 | CH₃ | 3-(2-cyanobenzyloxy)-phenyl | |
| 3.102 | CH₃ | 3-(4-nitrobenzyloxy)-phenyl | |
| 3.103 | CH₃ | 3-(2-nitrobenzyloxy)-phenyl | |
| 3.104 | CH₃ | 3-(phenylethoxy)-phenyl | |
| 3.105 | CH₃ | 3-(phenoxy-methyl)-phenyl | |
| 3.106 | CH₃ | 3-(3-chlorophenoxymethyl)-phenyl | |
| 3.107 | CH₃ | phenyl-CH₂-O-N=C(CH₃)-phenyl | |
| 3.108 | CH₃ | phenyl-CH₂-O-N=C(CH₃)-(3-chlorophenyl) | |

TABLE 3-continued

Structure:
H3C—(pyrimidine with R1, N, N, O—R3)—C(COOCH3)=CH—OCH3

| Comp. No. | R₁ | R₃ | physical data ¹H-NMR or/and m.p. |
|---|---|---|---|
| 3.109 | CH₃ | 3-(2,5-dimethylphenoxymethyl)-phenyl | |
| 3.110 | CH₃ | 4-[(3-(1-(methoxyimino)ethyl)phenoxy)methyl]phenyl | |
| 3.111 | CH₃ | 4-[(3-(1-(allyloxyimino)ethyl)phenoxy)methyl]phenyl | |
| 3.112 | CH₃ | 4-[(4-(1-(methoxyimino)ethyl)phenoxy)methyl]phenyl | |
| 3.113 | CH₃ | 4-[(4-(1-(allyloxyimino)ethyl)phenoxy)methyl]phenyl | |
| 3.114 | CH₃ | 4-[1-((3-chlorobenzyl)oxyimino)ethyl]phenyl | |
| 3.115 | CH₃ | 4-[1-((2,5-dichlorobenzyl)oxyimino)ethyl]phenyl | |
| 3.116 | CH₃ | 4-[1-((2,5-dimethylbenzyl)oxyimino)ethyl]phenyl | |
| 3.117 | CH₃ | 4-[1-((2-chlorobenzyl)oxyimino)ethyl]phenyl | |
| 3.118 | CH₃ | 4-[1-((4-nitrobenzyl)oxyimino)ethyl]phenyl | |
| 3.119 | CH₃ | 4-[1-((2-nitrobenzyl)oxyimino)ethyl]phenyl | |

TABLE 3-continued

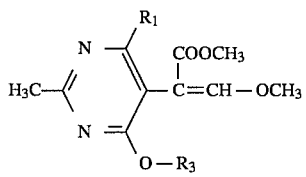

| Comp. No. | R₁ | R₃ | physical data $^1$H-NMR or/and m.p. |
|---|---|---|---|
| 3.120 | CH₃ | [phenyl-C(CH₃)=N—O-(3,4-dichlorobenzyl)] | |
| 3.121 | CH₃ | [phenyl-C(CH₃)=N—O-(2,4-dichlorobenzyl)] | |
| 3.122 | CH₃ | [phenyl-C(CH₃)=N—O-benzyl] | |
| 3.123 | CH₃ | [phenyl-C(CH₃)(O-)-(4-Cl-phenyl)] | |
| 3.124 | CH₃ | [phenyl-C(CH₃)-O-(4-Cl-phenyl)] | |
| 3.125 | CH₃ | 3-(3-thienyl)-phenyl | |
| 3.126 | CH₃ | 3-(2-naphthyl)-phenyl | |
| 3.127 | CH₃ | 3-(4-phenyl)-pheny) | |
| 3.128 | CH₃ | 3-(2-pyridyl)-phenyl | |

EXAMPLE A: Activity against Powdery Mildew

*Sphaerotheca fuliginea:*

Plants of *Cucumis sativus* (cucumber), 7 days old (cotyledon stage), are sprayed to near run off with a suspension containing 100 mg/l of active ingredient. The deposit is then allowed to dry. One day later, the treated plants are inoculated with a spore suspension containing 1×10⁵/ml of freshly collected conidia of Sphaerotheca_fuliginea and then incubated in the greenhouse for 7 days at +24° C. and 60% r.h.

The efficacy of the test compounds is determined by comparing the degree of fungal attack with that on untreated, similarly inoculated check plants. In this test compounds 1.03; 1.05; 1.07; 1.08; 1.13; 1.45; 1.46; 1.47; 1.48; 1.49; 1.50; 1.58; 1.59; 1.61; 1.87; 1.90; 1.91; 1.93; 1.122; 2.03; 2.45; 2.48; 2.58; 2.73; 2.75; 2.88; 2.90; 2.91; 2.93; 3.03; 3.05; 3.07 and 3.48; showed an efficacy of more than 90%.

Similar methods are used to test the compounds against the following pathogens:

*Podosphaera leucotricha* on apple,
*Erysiphe graminis* on wheat and barley (dry inoculation),
*Uncinula necator* on grape.

EXAMPLE B: Activity against Rust, Scab, Pyrenophora, Leptosphaeria

*Uromyces appendiculatus:*

Plants of *Phaseolus vulgaris* (pole bean), 14 days old (2 leaves stage), are sprayed to near run off with a suspension containing 100 mg/l of the active ingredient. The deposit is then allowed to dry. One day later, the treated plants are inoculated with a spore suspension containing 1×10⁵ /ml of freshly collected spores of Uromyces_appendiculatus. Incubation is performed for 3 days in a high humidity cabinet at +23° C. and >95% r.h. and thereafter during 10 days at +24° C. and 60% r.h.

The efficacy the compounds is determined by comparing the degree of fungal attack with that on untreated, similarly inoculated check plants. In this test compounds 1.03; 1.05; 1.07; 1.08; 1.13; 1.45; 1.46; 1.47; 1.48; 1.49; 1.50; 1.58; 1.59; 1.61; 1.87; 1.90; 1.91; 1.93; 1.122; 2.03; 2.45; 2.48; 2.58; 2.73; 2.75; 2.88; 2.90; 2.91; 2.93; 3.03; 3.05; 3.07 and 3.48 showed an efficacy of at least 90%.

Similar methods are used to test the compounds against the following pathogens:

*Puccinia triticina* on wheat (plants 10 days old),

*Pyrenophora graminca* on barley,

*Leptosphaeria nodorum* on wheat,

*Venturia inaequalis* on apple (plants 21 days old; the spore suspension contains 1% malt).

EXAMPLE C: Activity against Downy Mildew

Plants of *Lycopersicon esculentum* (tomato) with 6 leaves, are sprayed to near run off with a spray suspension containing 100 mg/l of the active ingredient. The deposit is then allowed to dry. 1 day later, the treated plants are inoculated with a spore suspension containing $1 \times 10^5$/ml of freshly collected sporangia of Phytophthora infestans and then incubated for 7 days in a high humidity cabinet at +18° C. and >95% r.h. The efficacy of the test compounds is determined by comparing the degree of fungal attack with that on untreated, similarly inoculated check plants. In this test compounds 1.03, 1.13, 1.48, 158 and 1.61 should efficacy of at least 90%.

A similar method is used to test the compounds against *Plasmopara viticola* on grape vine.

EXAMPLE D: Activity after Seed Treatment

The compounds of the invention may also be used for seed treatment. The advantageous fungitidal activity is established by in vitro tests with the following pathogens:

*Pyrenophora graminca,*

*Ustilago nuda,*

*Gefiachia nivalis,*

*Leptoshpaefia nodorum.*

Autoclaved wheat seeds are inoculated with spores or mycelium of the pathogens and coated with different concentrations of the test compounds resulting in dosages of 50 g a.i./100 kg seed. The treated seeds are then placed on agar plates and the pathogens allowed to grow for 3–8 days at +24° C. in the dark.

The efficacy of the test compounds is determined by comparing the degree of fungal growth emerging from treated and untreated inoculated seeds.

To evaluate the crop plant tolerance of the compounds, healthy seeds of wheat and barley are coated with the dosages mentioned above. The seeds are then allowed to germinate in petri dishes on moist filter paper in high humidity at +18° C. for 10 days. Plant damage is recorded, comparing the growth of treated and untreated seedlings.

In this test compounds of formula I showed an efficacy of at least 90% against *Pyrenophora graminea*.

We claim:

1. A compound of the formula (I)

wherein $R_1$ is hydrogen, methyl, ethyl or trifluoromethyl;

$R_2$ is hydrogen, methyl, ethyl, $C_{1-4}$alkylthio, $C_{1-4}$alkoxy, or di-$C_{1-4}$-alkylamino;

$R_3$ is $C_{1-10}$alkyl, $C_{1-10}$haloalkyl, aryl, heteroaryl, aryl-$C_{1-4}$alkyl, heteroaryl-$C_{1-4}$alkyl, aryloxy-$C_{1-4}$alkyl, aryyloxyaryl, arylaryl, heteroarylaryl, aryl-$C_{1-4}$aryloxyaryl, aryl$C_{1-4}$alkoxy-$C_{1-4}$alkyl, heteroaryloxyaryl, aryloxy-$C_{1-4}$alkylaryl or aryl substituted by a group selected from —C(CH$_3$)=N—O—CH$_2$—aryl, —C(CH$_3$)=N—C$_{1-4}$alkoxy, —C(CH$_3$)=N-OCH(CH$_3$)—aryl, —C(CH$_3$)=N—C$_{3-4}$alkenyloxy, —C(CH$_3$)=N—C$_{3-4}$alkynyloxy or —CH$_2$—O—N=C(CH$_3$)—aryl;

wherein each of the aromatic rings of $R_3$ may be optionally independently substituted by one to five substituents selected from the group consisting of halogen, $C_{1-4}$alkyl, $C_{1-4}$alkoxy, $C_{3-7}$cycloalkyl, $C_{1-4}$haloalkyl, $C_{1-4}$haloalkoxy, cyano, nitro, aryl, aryloxy and aryl-$C_{1-4}$alkoxy; and wherein aryl is independently phenyl or naphthyl and heteroaryl is independently pyridyl, pyrimidinyl, pyridazinyl, quinolinyl, quinazolinyl, thienyl or furyl.

2. A compound according to claim 1 wherein $R_3$ is $C_{1-10}$alkyl, phenyl, naphthyl, pyridyl, pyrimidinyl, thienyl, furyl, benzyl, phenethyl, phenoxy-$C_{1-4}$alkyl, or benzyloxy-$C_{1-4}$alkyl wherein each of the aromatic rings of $R_3$ may be optionally substituted by one to two substituents selected from the group consisting of halogen, $C_{1-4}$alkyl, $C_{1-4}$alkoxy, $C_{1-4}$haloalkyl, $C_{1-4}$haloalkoxy, cyano, nitro, aryloxy, aryl-$C_{1-4}$alkoxy and aryl.

3. A compound according to claim 2 wherein $R_3$ is $C_{1-4}$alkyl, phenyl, benzyl, phenoxyethoxy, benzyloxyethoxy, biphenyl, $C_{1-4}$alkylphenyl, $C_{1-4}$haloalkylphenyl or halophenyl.

4. A compound according to claim 1 wherein $R_2$ is hydrogen.

5. A compound according to claim 1 wherein $R_1$ is methyl.

6. A compound according to claim 1, of formula Ia wherein $R_2$ is hydrogen, methyl or methylthio;

$R_4$ is hydrogen or methyl;

$R_5$ is hydrogen, aryl, heteroaryl, $C_{1-4}$alkyl, —CH$_2$—O—$C_{1-4}$alkyl, —CH$_2$—O—$C_{3-7}$cycloalkyl, —CH$_2$—O—aryl, —CH$_2$—O—CH$_2$—aryl, —C(CH$_3$)=N—$C_{1-4}$alkoxy, —C(CH$_3$)N—$C_{3-4}$=alkenyloxy, —C(CH$_3$)=N—OCH$_2$—aryl;

wherein aryl may be optionally substituted with one or two substituents independently selected from the group consisting of halogen, $C_{1-4}$alkyl, $C_{1-4}$alkoxy, and cyano;

or is 2-pyridyloxy optionally substituted with one or two substituents independently selected from the group consisting of $C_{1-4}$alkyl, halogen and nitro;

or is phenoxy optionally substituted by one to three substituents selected from the group consisting of halogen, $C_{1-4}$alkyl, $C_{1-4}$alkoxy, $C_{1-4}$haloalkyl, $C_{1-4}$haloalkoxy, cyano and nitro;

or is benzyloxy optionally substituted by one to five subsituents independently selected from the group consisting of halogen or $C_{1-4}$alkyl or one to three substituents independently selected from the group consisting of halogen, $C_{1-4}$alkyl, nitro, cyano and $C_{1-4}$haloalkoxy.

7. A compound according to claim 6 wherein $R_5$ is hydrogen, phenyl, $C_{1-4}$alkyl, phenoxymethyl, benzyloxyphenyl, —C(CH$_3$)—N—OCH$_3$, phenoxy, benzyloxy, —C(CH$_3$)=N—allyloxy, —C(CH$_3$)=N—benzyloxy wherein the phenyl groups are optionally substituted by one or two substituents independently selected from the group consisting of cyano, methyl, methoxy, nitro and halogen.

8. The compound according to claim 1 methyl α-[6-methyl-4-(3 -trifluoromethylphenoxy)-5-pyrimidinyl]-β-methoxyacrylate.

9. The compound according to claim 1 methyl α-[6-methyl-4-(3-(2 -cyanophenoxy)-phenoxy)-5-pyrimidinyl]-β-methoxyacrylate.

10. The compound according to claim 1 methyl α-[6-methyl-4-(3-(1 -methoximinoethyl)-phenoxy)-5-pyrimidinyl]-β-methoxyacrylate.

11. The compound according to claim 1 methyl α-[6-methyl-4-(3 -isopropylphenoxy)-5-pyrimidinyl]-β-methoxyacrylate.

12. The compound according to claim 1 methyl α-[6-methyl-4-(3 -phenylphenoxy)-5-pyrimidinyl]-β-methoxyacrylate.

13. The compound according to claim 1 methyl α-[2-methyl-4-(3 -trifluoromethylphenoxy)-5-pyrimidinyl]-β-methoxyacrylate.

14. The compound according to claim 1 methyl α-[2-methylthiol-6-methyl-4-( 3-trifluoromethylphenoxy)-5-pyrimidinyl]-β-methoxyacrylate.

15. The compound according to claim 1 methyl α-[2,6-dimethyl-4-(3 -phenylphenoxy)-5-pyrimidinyl]-β-methoxyacrylate.

16. The compound according to claim 1 methyl α-[2,6-dimethyl-4-(3-methyl -5-isopropylphenoxy)-5-pyrimidinyl] -β-methoxyacrylate.

17. The compound according to claim 1 methyl α-[6-methyl-4-(3-(2 -methylbenzyloxy)-phenoxy)-5-pyrimidinyl]-β-methoxyacrylate.

18. A method of combatting phytopathogenic fungi comprising applying to the fungi or their habitat a fungicidally effective amount of a compound of formula I according to claim 1.

19. A fungicidal composition comprising an effective amount of a compound of formula I as stated in claim 1 and an agriculturally acceptable diluent.

* * * * *